United States Patent
Yamamoto et al.

(10) Patent No.: US 11,298,370 B2
(45) Date of Patent: Apr. 12, 2022

(54) PROPHYLACTIC OR THERAPEUTIC AGENT FOR INFLAMMATORY BOWEL DISEASE

(71) Applicants: Hirofumi Yamamoto, Osaka (JP); Masaki Mori, Toyonaka (JP)

(72) Inventors: Hirofumi Yamamoto, Osaka (JP); Masaki Mori, Toyonaka (JP)

(*) Notice: Subject to any disclaimer, the term of this patent is extended or adjusted under 35 U.S.C. 154(b) by 0 days.

(21) Appl. No.: 16/607,681

(22) PCT Filed: Apr. 24, 2018

(86) PCT No.: PCT/JP2018/016686
§ 371 (c)(1),
(2) Date: Oct. 23, 2019

(87) PCT Pub. No.: WO2018/199121
PCT Pub. Date: Jan. 11, 2018

(65) Prior Publication Data
US 2020/0188423 A1    Jun. 18, 2020

(30) Foreign Application Priority Data
Apr. 24, 2017  (JP) .............. JP2017-085318

(51) Int. Cl.
| | | |
|---|---|---|
| *A61K 31/7105* | (2006.01) | |
| *A61P 43/00* | (2006.01) | |
| *C12N 15/113* | (2010.01) | |
| *A61K 47/51* | (2017.01) | |
| *A61P 1/00* | (2006.01) | |

(Continued)

(52) U.S. Cl.
CPC ........ *A61K 31/7105* (2013.01); *A61K 9/0019* (2013.01); *A61K 9/14* (2013.01); *A61K 47/51* (2017.08); *A61P 1/00* (2018.01)

(58) Field of Classification Search
CPC ...... A61K 31/7105; A61K 9/14; A61K 47/02; C12N 15/113; A61P 43/00; A61P 1/04
See application file for complete search history.

(56) References Cited

U.S. PATENT DOCUMENTS

| | | | |
|---|---|---|---|
| 9,889,155 B2 | 2/2018 | Yamamoto et al. | |
| 2016/0071936 A1 | 3/2016 | Eon et al. | |

FOREIGN PATENT DOCUMENTS

| | | |
|---|---|---|
| JP | 2003-068592 A | 3/2003 |
| JP | 2006-509838 A | 3/2006 |
| JP | 2016-119428 A | 6/2016 |

(Continued)

OTHER PUBLICATIONS

Hossain et al. (Journal of Controlled Release, 2010 Vol. 147:101-108).*

(Continued)

*Primary Examiner* — Terra C Gibbs
(74) *Attorney, Agent, or Firm* — Knobbe, Martens, Olson & Bear, LLP

(57) ABSTRACT

The purpose of the present invention is to provide a therapeutic agent which is for inflammatory bowel disease and exhibits superior prophylactic or therapeutic effects on inflammatory bowel disease by using miR-29a and/or miR-29b. The prophylactic or therapeutic agent for inflammatory bowel disease comprises composite particles in which miR-29a and/or miR-29b is/are carried on carbonate apatite particles, and said agent is administered systemically.

11 Claims, 15 Drawing Sheets

Specification includes a Sequence Listing.

(51) Int. Cl.
*A61K 9/00* (2006.01)
*A61K 9/14* (2006.01)

(56) References Cited

FOREIGN PATENT DOCUMENTS

| JP | 2016-522988 A | 8/2016 |
|---|---|---|
| WO | WO 2004/043495 A1 | 5/2004 |

OTHER PUBLICATIONS

Wu et al. (PLOS One, 2015 vol. 10(3):1-21).*
Ardizzone, et al., 2005 "Biologic Therapy for Inflammatory Bowel Disease", Drugs, 65: 2253-2286.
Bouma, et al., 2003 "The Immunological and Genetic Basis of Inflammatory Bowel Disease", Nature Reviews Immunology, 3: 521-533.
Brain, et al., 2013 "The Intracellular Sensor NOD2 Induces MicroRNA-29 Expression in Human Dendritic Cells to Limit IL-23 Release", Immunity, 39: 521-536.
Fiocchi, 1998 "Inflammatory Bowel Disease: Etiology and Pathogenesis", Gastroenterology, 115: 182-205.
Guo, et al., 2016 "RNA interference-based nanosystems for inflammatory bowel disease therapy", International Journal of Nanomedicine, 11: 5287-5310.
Hata, et al., 2015 "Laparoscopic surgery for ulcerative colitis: a review of the literature", Surgery Today, 45: 933-938.
International Search Report in International Application No. PCT/JP2018/016686, dated Jul. 10, 2018.
Kalla, et al., 2015 "MicroRNAs: new players in IBD", Gut, 64: 504-517.
Oldenburg, et al., 2007 "Biological therapies in inflammatory bowel disease: top-down or bottom-up?", Curr Opin Gastroenterol, 23: 395-399.
Strober, et al., 2007 "The Fundamental Basis of Inflammatory Bowel Disease", J Clin Invest, 117(3):514-521.
Japanese Office Action in Japanese Patent Application No. 2018-004027 dated Jul. 27, 2021.
Yamada, Hideaki, et al., "Fabrication and fundamental characterizations of tiled clones of single-crystal diamond with 1-inch size," Diamond & Related Materials 24 (2012), pp. 29-33.

* cited by examiner

FIG. 14

PROPHYLACTIC OR THERAPEUTIC AGENT FOR INFLAMMATORY BOWEL DISEASE

TECHNICAL FIELD

The present invention relates to a prophylactic or therapeutic agent for an inflammatory bowel disease. More specifically, the present invention relates to a prophylactic or therapeutic agent for an inflammatory bowel disease including miR-29a and/or miR-29b.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 31941257_1.TXT, the date of creation of the ASCII text file is Jan. 22, 2020, and the size of the ASCII text file is 2.13 KB.

BACKGROUND ART

Inflammatory bowel disease (IBD) is a chronic inflammatory disease in a gastrointestinal tract, and is roughly classified into ulcerative colitis and Crohn's disease (Non-Patent Documents 1 to 3). Particularly in the United States and Europe, the incidence rate of inflammatory bowel disease has increased (Non-Patent Document 2), and there have been serious problems of a high recurrence rate of inflammatory bowel disease. Conventionally, acute inflammatory bowel diseases have been treated basically using anti-inflammatory drugs, immunosuppressive drugs, glucocorticoids and the like (Non-Patent Document 4). In addition, as a new treatment method for inflammatory bowel disease, procedures for inhibiting a mucosal inflammatory pathway which targets a proinflammatory cytokine such as TNF-α, or a cell surface receptor for the proinflammatory cytokine have been proposed (Non-Patent Documents 5 and 6).

However, under the current circumstances, even after treatment of inflammatory bowel disease by drug administration, about 30% of patients still require surgical treatments due to severe inflammation, intestinal stenosis, or toxic megacolon.

Although pathogeneses and pathological conditions of inflammatory bowel disease have not been fully elucidated, but it is considered that a plurality of factors such as oxidation stress disorders, congenital and adaptive immune disorders, genetic factors, intestinal bacteria, and dietary habits are complexly involved in the pathogeneses and pathological conditions.

On the other hand, nucleic acid medicines are attracting attention as next-generation treatment methods for various diseases. Among nucleic acid medicines, a microRNA (miRNA) is a small non-coding RNA, and refers to an RNA molecule which regulates expression of a plurality of target genes mainly by binding to a complementary sequence in a 3'-UTR region. Recent researches have demonstrated presence of miRNAs involved in epithelial barrier functions (miRs-7, 21, 150), autophagy (miRs-13A, 93, 106, 142-3p), NF-kB signaling pathways (miRs-126, 146a), and IL23/Th17 inflammatory axes (miRs-20, 23a, 29b, 155), and the like (Non-Patent Document 7). Thus, these miRNAs or anti-miRNAs are expected as therapeutic tools for inflammatory bowel disease. However, under the current circumstances, the diseases for which effective treatments are recognized with nucleic acid medicines using miRNAs—are conventionally limited to eye disease, hyperlipidemia and myodegeneration disease.

In addition, for nucleic acid medicines using miRNAs, it is important to efficiently deliver the miRNAs to targeted cells in vivo. Conventionally, liposomes have been widely used for delivering miRNAs into cells in vitro. However, for treatment of inflammatory bowel disease, a technology to efficiently deliver miRNAs to an inflammatory lesion in vivo has not been established.

On the other hand, it has been a report that colitis induced by dextran sulfate (DSS) is exacerbated in a miR-29a and miR-29b-knocked-out mice (Non-Patent Document 8), and the miR-29a and miR-29b are expected as therapeutic drugs for inflammatory bowel disease. However, as described above, a technology to efficiently deliver the miRNA to the inflammatory bowel disease lesion in vivo has not been developed, and in order to implement the miR-29a and miR-29b as therapeutic drugs for inflammatory bowel disease, it is essential to establish an in vivo delivery technology (Non-Patent Document 9).

PRIOR ART DOCUMENT

Non-Patent Documents

Non-Patent Document 1: Nat Rev Immunol 3: 521-33, 2003
Non-Patent Document 2: J Clin Invest 117: 514-21, 2007
Non-Patent Document 3: Gastroenterology 115: 182-205, 1998
Non-Patent Document 4: Drugs 65: 2253-86, 2005
Non-Patent Document 5: Curr Opin Gastroenterol 23: 395-9, 2007
Non-Patent Document 6: Surgery today 45: 933-8, 2015
Non-Patent Document 7: Gut 64 (6): 1008, 2015
Non-Patent Document 8: Immunity 39: 521-36, 2013.
Non-Patent Document 9: Int J Nanomedicine 11: 5287-5310, 2016.

SUMMARY OF THE INVENTION

Problems to be Solved by the Invention

An object of the present invention is to provide a prophylactic or therapeutic agent which is for inflammatory bowel disease and exhibits superior prophylactic or therapeutic effects on inflammatory bowel disease by using miR-29a and/or miR-29b.

Means for Solving the Problem

Carbonate apatite particles are known to have an action of delivering nucleic acids into cells (Japanese Patent Laid-open Publication No. 2007-63194). Since the carbonate apatite particles have not been known to have an action to accumulate in inflamed tissues, it is considered from the prior art that even when composite particles having the miR-29a and/or miR-29b carried on carbonate apatite particles are systemically administered, the miR-29a and/or miR-29b cannot be efficiently delivered to an inflammatory bowel disease lesion. Thus, the inventors and the like of the present invention tried to locally administer the composite particles having the miR-29a and/or miR-29b carried on the carbonate apatite particles to the inflammatory bowel disease lesion, and a result, improvement of the inflammatory bowel disease was hardly observed (see Reference Test Example 5 described later).

Under such a situation, as a result of intensive studies by the present inventors, it has been found that when a composite particle having miR-29a and/or miR-29b carried on a carbonate apatite particle is systemically administered, a part of the miRNA is taken into not only the inflammatory bowel disease lesion but also dendritic cells localizing on a mucosa of the lesion, and inflammatory bowel disease could be effectively improved by an action of the miRNA uptake directly into the lesion and an action of the dendritic cells having the taken miRNA. That means, it has been found that systemic administration of the composite particle having miR-29a and/or miR-29b carried on the carbonate apatite particle causes the miRNAs to act not only on the inflammatory bowel disease lesion but also on the dendritic cells involved in an initial immunoreaction of inflammation, so that a therapeutic effect for inflammatory bowel disease is remarkably improved. On the basis of this finding, the present invention has been completed by further multiple studies.

That is, the present invention provides inventions in the following aspects.

Item 1. A prophylactic or therapeutic agent for an inflammatory bowel disease, wherein the agent comprises composite particles each having miR-29a and/or miR-29b carried on a carbonate apatite particle, and the agent is administered systemically.

Item 2. The prophylactic or therapeutic agent for an inflammatory bowel disease according to Item 1, which is administered through intravascular administration or subcutaneous administration.

Item 3. The prophylactic or therapeutic agent for an inflammatory bowel disease according to Item 1 or 2, wherein the carbonate apatite particles have an average particle diameter of 400 to 3000 nm.

Item 4. Use of composite particles each having miR-29a and/or miR-29b carried on a carbonate apatite particle for the manufacture of a prophylactic or therapeutic agent for an inflammatory bowel disease, wherein the agent is administered systemically.

Item 5. The use according to Item 4, wherein the systemic administration is intravascular administration or subcutaneous administration.

Item 6. The use according to Item 4 or 5, wherein the carbonate apatite particles have an average particle diameter of 400 to 3000 nm.

Item 7. An inflammatory bowel disease prophylactic or therapeutic method, comprising systemically administering composite particles each having miR-29a and/or miR-29b carried on a carbonate apatite particle to a patient in need of prophylaxis or therapy of inflammatory bowel disease.

Item 8. The method according to Item 7, wherein the systemic administration is intravascular administration or subcutaneous administration.

Item 9. The inflammatory bowel disease prophylactic or therapeutic method according to Item 7 or 8, wherein the carbonate apatite particles have an average particle diameter of 400 to 3000 nm.

Advantages of the Invention

According to the prophylactic or therapeutic agent for an inflammatory bowel disease according to the present invention, systemic administration of the composite particle having miR-29a and/or miR-29b carried on the carbonate apatite particle causes the miRNA to be taken into not only the inflammatory bowel disease lesion but also the dendritic cells, so that a remarkably excellent therapeutic effect can be exhibited.

The miR-29a and/or miR-29b taken directly into the inflammatory bowel disease lesion contribute to alleviation or curing of symptoms of the lesion. In addition, the dendritic cells having the taken miR-29a and/or miR-29b contribute to the therapeutic effect for inflammatory bowel disease by decreasing expression levels of cytokines (IL-6 and TGF-β) involved in differentiation of naive T cells into Th-17 cells and cytokines (IL12 p40 and IL23 p19) which activate and lead the Th-17 cells to pathogenic Th-17 cells. That means, in relation to the prophylactic or therapeutic agent for an inflammatory bowel disease according to the present invention, systemic administration of the composite particle having miR-29a and/or miR-29b carried on the carbonate apatite particle can act not only directly on the lesion but also on the dendritic cells, so that a remarkably excellent therapeutic effect can be exhibited. The dendritic cells are important factors involved in the initial immunoreaction of inflammatory bowel disease. By inhibiting the dendritic cells, the prophylactic or therapeutic agent for an inflammatory bowel disease according to the present invention can effectively suppress spread of inflammation on the entire intestinal tract via interferon signals.

BRIEF DESCRIPTION OF THE DRAWINGS

FIG. 14 is a diagram illustrating a result of measuring take-in levels of the MIRTX in CD11c-positive cells (dendritic cells) and CD11c-negative cells isolated from mucosas of large intestines recovered after subcutaneously administrating a MIRTX/sCA composite to DSS-induced mouse enteritis models, in Reference Test Example 4.

EMBODIMENTS OF THE INVENTION

Figure 1:
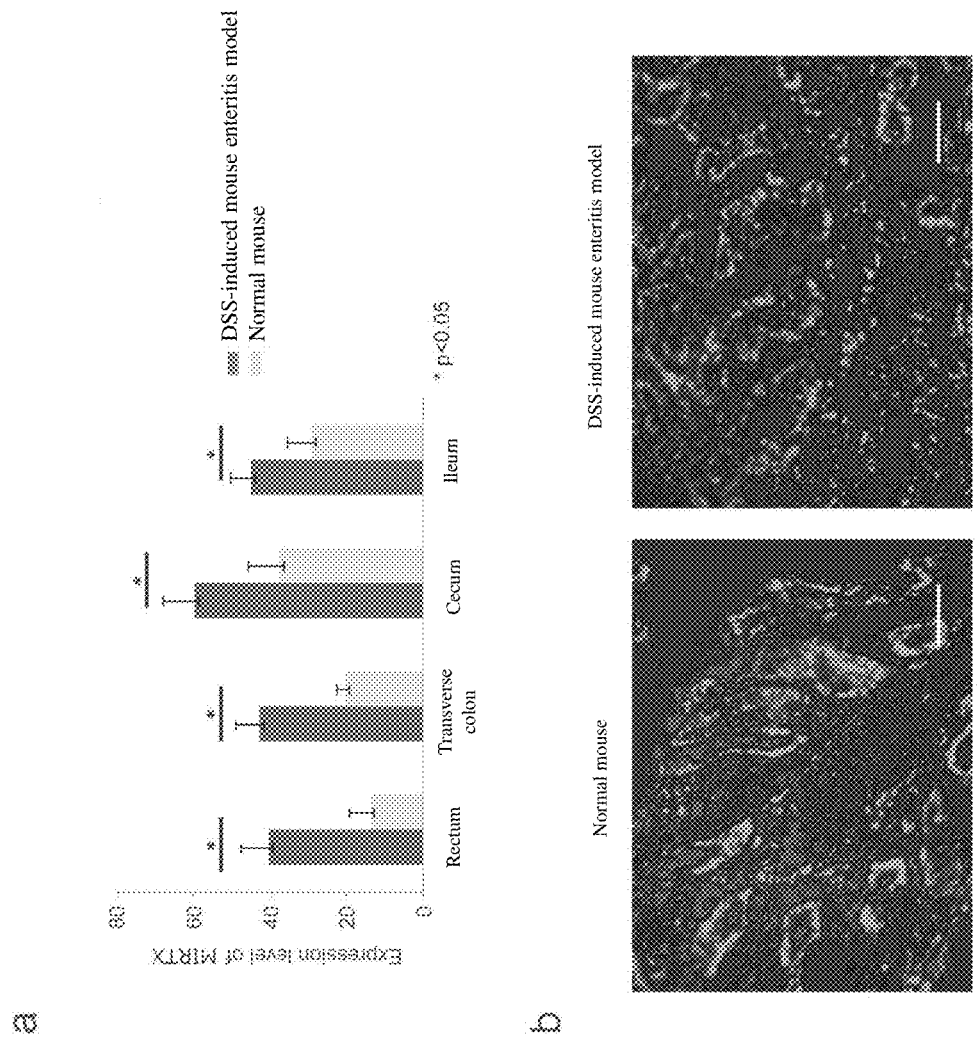
FIG. 1. (a) is a diagram illustrating a result of Reference Test Example 1, which presents a result of measuring take-in levels of MIRTX in rectums, transverse colons, cecums, and ileums after intravenously administering the MIRTX (miR-29b derivative (artificial miRNA))/sCA composite to DSS-induced mouse enteritis models. (b) is a diagram illustrating a result of Reference Test Example 1, which presents images indicating results of fluoroscopically observing intestines nuclear-stained after intravenously administering an Alexa647-miRNA/sCA composite to DSS-elicited mouse enteritis models.

The prophylactic or therapeutic agent according to the present invention is an agent to be used for preventing or treating inflammatory bowel disease, which characteristically contains the composite particles each having miR-29a and/or miR-29b carried on the carbonate apatite particle and is systemically administered. Hereinafter, the preventive or therapeutic agent according to the present invention will be described in detail.

miRNA

The prophylactic or therapeutic agent according to the present invention contains the miR-29a and/or miR-29b as the miRNA. Although there is a report that colitis induced by dextran sulfate (DSS) is exacerbated in miR-29a and miR-29b-knocked-out mice (Non-Patent Document 8), it has not been conventionally known that these miRNAs have an action of decreasing expression levels of cytokines such as IL-6, TGF-β, IL12 p40 and IL23 p19 in dendritic cells.

The miR-29a used in the present invention may be a mature miRNA, or a hairpin type precursor miRNA (pri-miRNA), or a pre-miRNA in which a part of the pri-miRNA is cleaved. The pri-miRNA and the pre-miRNA are processed in cells to become a mature miR-29a. A double-stranded precursor composed of an RNA having a complementary base sequence may be formed. The double strand of the double-stranded RNA is untied in the cell to release the mature miR-29a. In addition, a base sequence of the hairpin type precursor miR-29a may be set so that the precursor is processed in vivo to generate the mature miR-29a, and such a base sequence can be appropriately set by those skilled in the art.

An origin of the miR-29a used in the present invention may be appropriately set depending on a kind of an animal to which the miR-29a is applied. For example, when the miR-29a is used for treating human inflammatory bowel disease, a human-derived miR-29a may be used. Specific examples of the human-derived miR-29a used in the present invention include the following mature miR-29a. Incidentally, a base sequence of a mouse-derived miR-29a is the same as that of the human-derived miR-29a.

```
Mature has-miR-29a (sense):
                                      (SEQ ID NO: 1)
5'-UAG CAC CAU CUG AAA UCG GUU A-3'

Mature has-miR-29a (antisense):
                                      (SEQ ID NO: 2)
5'-UAA CCG AUU UCA GAU GGU GCU A-3'
```

Also, the miR-29b used in the present invention may be a mature miRNA, or a hairpin type precursor miRNA (pri-miRNA), or a pre-miRNA in which a part of the pri-miRNA is cleaved. The pri-miRNA and the pre-miRNA are processed in cells to become a mature miR-29b. A double-stranded precursor composed of an RNA having a complementary base sequence may be formed. The double strand of the double-stranded RNA is untied in the cell to release the mature miR-29b. In addition, a base sequence of the hairpin type precursor miR-29b may be set so that the precursor is processed in vivo to generate the mature miR-29b, and such a base sequence can be appropriately set by those skilled in the art.

An origin of the miR-29b used in the present invention may be appropriately set depending on a kind of an animal to which the miR-29b is applied. For example, when the miR-29b is used for treating human inflammatory bowel disease, a human-derived miR-29b may be used. Specific examples of the human-derived miR-29b used in the present invention include the following mature miR-29b. Incidentally, a base sequence of a mouse-derived miR-29b is the same as that of the human-derived miR-29b.

```
Mature has-miR-29b (sense):
                                      (SEQ ID NO: 3)
5'-UAG CAC CAU UUG AAA UCA GUG UU-3'

Mature has-miR-29b (antisense):
                                      (SEQ ID NO: 4)
5'-AAC ACU GAU UUC AAA UGG UGC UA-3'
```

For the miR-29a and/or miR-29b, generally various modifications may be applied to nucleic acids as necessary, to provide a degradation resistance to enzymes, and the like. Examples of such modifications include sugar chain moiety modification such as 2'-O-methylation; base moiety modification; phosphate moiety modification such as amination, lower alkyl-amination and acetylation; and the like.

In the prophylactic or therapeutic agent according to the present invention, either the miR-29a or the miR-29b may be used as the miRNA, or a combination of the miR-29a and the miR-29b may be used.

Carbonate Apatite Particle

A carbonate apatite has a structure in which a hydroxyl group of hydroxyapatite ($Ca_{10}(PO_4)_6(OH)_2$) is partially substituted with $CO_3$, and the carbonate apatite is a compound represented by a general formula $Ca_{10-m}X_m(PO_4)_6(CO_3)_{1-n}Y_n$. Herein, X is an element capable of partially replacing Ca in the carbonate apatite, and examples of X include Sr, Mn, rare earth elements, and the like. m is a positive number of normally 0 or more and 1 or less, preferably 0 or more and 0.1 or less, more preferably 0 or more and 0.01 or less, even more preferably 0 or more and 0.001 or less. Y is a group or an element capable of partially replacing $CO_3$ in the carbonate apatite, and examples of Y include OH, F, Cl, and the like. n is a positive number of normally 0 or more and 0.1 or less, preferably 0 or more and 0.01 or less, more preferably 0 or more and 0.001 or less, even more preferably 0 or more and 0.0001 or less.

An average particle diameter of the carbonate apatite particle used in the present invention is not particularly limited as long as the size of the carbonate apatite particle allows the particle to be administered into a living body and to transfer into cells. However, it is possible to preferably use a particle having an average particle diameter larger than the average particle diameter (50 nm or smaller) of the conventional carbonate apatite particle used as a nucleic acid carrier to be administered to blood, because the carbonate apatite particles are taken in the dendritic cells mainly by phagoptosis. Specifically, the average particle diameter of the carbonate apatite particle used in the present invention is normally larger than 50 nm (e.g. larger than 50 nm and 3000 nm or smaller), preferably 100 to 3000 nm, more preferably 100 to 2000 nm, even more preferably 200 to 2000 nm or 400 to 3000 nm, particularly preferably 400 to 2000 nm.

Incidentally, the average particle diameter of the carbonate apatite is measured by a dynamic light scattering particle measurement (DLS). If there are huge particles (e.g. particle diameters of 5 μm or larger) unsuitable for measurement using DLS, the particles are excluded from a measurement range. Additionally, in the present specification, the particle diameter means a particle diameter of independent particle recognizable as a separate particle when measured with a scanning probe microscope. Therefore, when a plurality of particles are aggregated, an aggregate of the particles is determined as one particle.

The carbonate apatite particle can be obtained according to a known method. For example, the carbonate apatite particle can be prepared by allowing calcium ions, phosphate ions and hydrogencarbonate ions to coexist in an aqueous solution. Each ion concentration in the aqueous solution is not particularly limited as long as the carbonate apatite particle can be formed, and the ion concentration can be appropriately set with reference to the following description.

The calcium ion concentration in the aqueous solution is normally 0.1 to 1000 mM, preferably 0.5 to 100 mM, more preferably 1 to 10 mM.

The phosphate ion concentration in the aqueous solution is normally 0.1 to 1000 mM, preferably 0.5 to 100 mM, more preferably 1 to 10 mM.

The hydrogencarbonate ion concentration in the aqueous solution is normally 1.0 to 10000 mM, preferably 5 to 1000 mM, more preferably 10 to 100 mM.

The sources for calcium ions, phosphate ions and hydrogencarbonate ions are not particularly limited as long as these ions can be supplied in the aqueous solution, but examples of the sources include water-soluble salts of these ions. Specifically, $CaCl_2$ can be used as the calcium ion source, $NaH_2PO_4 \cdot 2H_2O$ can be used as the phosphate ion source, and $NaHCO_3$ can be used as the carbonate ion source.

The aqueous solution for preparing the carbonate apatite particle may contain components other than the aforementioned each ion source and other substances as long as the carbonate apatite particle is formed. For example, fluorine ions, chlorine ions, Sr, Mn, polyethylene glycol (PEG) or the like may be added to the aforementioned compositions in an aqueous solution to partially substitute or modify Ca, $CO_3$ or the like in the carbonate apatite. However, an amount of the added fluorine ions, chlorine ions, Sr, Mn, PEG, or the like is preferably within a range that does not significantly affect a pH solubility and a particle diameter range of the formed composite particle. In addition, for the aqueous solution for preparing the carbonate apatite particle, water may be used as a base, but various media, buffers, and the like for cell culture may be used.

For preparing the carbonate apatite particle used in the present invention, an order of mixing each ion source and other substances in the aqueous solution is not particularly limited, and the aqueous solution may be prepared in any mixing order as long as the desired carbonate apatite particle can be obtained. For example, a first solution containing calcium ions and other substances is prepared, and separately a second solution containing phosphate ions and hydrogencarbonate ions is prepared, and the first solution and the second solution can be mixed to prepare an aqueous solution.

The carbonate apatite particle can be obtained by adjusting a pH of the aqueous solution containing each of the aforementioned ions to within a range of 6.0 to 9.0 and leaving (incubating) the aqueous solution for a certain period. The pH of the aqueous solution for forming the carbonate apatite particle is e.g. 7.0 to 8.5, preferably 7.1 to 8.5, more preferably 7.2 to 8.5, even more preferably 7.3 to 8.5, particularly preferably 7.4 to 8.5, most preferably 7.5 to 8.0.

A temperature condition of the aqueous solution for forming the carbonate apatite particle is not particularly limited as long as the carbonate apatite particle is formed, but the temperature is normally 4° C. or higher, preferably 25 to 80° C., more preferably 37 to 70° C. or higher.

An incubation time of the aqueous solution for forming the carbonate apatite particle is not particularly limited as long as the carbonate apatite particle is formed, but the incubation time is normally 1 minute to 24 hours, preferably 5 minutes to 1 hour. Whether or not the particle is formed can be confirmed e.g. by microscopic observation.

Furthermore, a method for controlling the average particle diameter of the carbonate apatite particle to within the above range is not particularly limited, but includes e.g. a method of ultrasonically vibrating the carbonate apatite particle formed in the aqueous solution. Specific examples of the ultrasonic vibration includes: a treatment in which a sample is ultrasonicated while bring an ultrasonic vibrator such as an ultrasonic crusher directly into contact with the sample; a treatment in which using an ultrasonic cleaner equipped with an ultrasonic vibrator and a water tank (cleaning tank), a liquid (e.g. water) is put into the water tank, a container (e.g. plastic tube) containing carbonate apatite particle is floated on the liquid, and an aqueous solution containing the carbonate apatite particle is ultrasonicated through the liquid; and the like. According to such ultrasonic vibration, the particle diameters of the carbonate apatite particles can be simply and efficiently fined to within the above range. Furthermore, the particle diameter of the carbonate apatite particle can also be adjusted to within the above range by separating the carbonate apatite particle having a desired particle diameter through a filter having a predetermined pore size after the ultrasonication.

A condition for the ultrasonic vibration is not particularly limited as long as the particle diameters can be controlled to within a predetermined range. For example, when using an ultrasonic cleaner equipped with an ultrasonic vibrator and a water tank (cleaning tank), the condition includes e.g. the following conditions.

Water bath temperature: e.g. 5 to 45° C., preferably 10 to 35° C., more preferably 20 to 30° C.

High frequency output: e.g. 10 to 500 W, preferably 20 to 400 W, more preferably 30 to 300 W, even more preferably 40 to 100 W Oscillatory frequency: e.g. 10 to 60 Hz, preferably 20 to 50 Hz, more preferably 30 to 40 Hz Treatment time: e.g. 30 seconds to 30 minutes, preferably 1 to 20 minutes, more preferably 3 to 10 minutes.

The type of the container containing the carbonate apatite particle used for the ultrasonic vibration is not limited as long as the particle can be fined to within a predetermined particle diameter range, and the type can be appropriately selected depending on a volume of the aqueous solution and an intended purpose. For example, a plastic tube having a capacity of 1 to 1000 ml can be used.

In addition, the ultrasonic vibration is preferably carried out in the presence of a dispersant (i.e. a state that the dispersant is added to an aqueous solution containing the carbonate apatite particle). This is because the ultrasonic vibration in an environment where the dispersant and the carbonate apatite particle coexist can provide a carbonate apatite nanoparticle having a finer particle diameter, and also suppress re-aggregation of the particles. A type of the dispersant is not particularly limited as long as the carbonate apatite particle can be dispersed, and any dispersant which is generally added to pharmaceuticals is allowed, but an example is albumin. The dispersant may be used alone or in combination of two or more kinds. A concentration of the dispersant in the aqueous solution containing the carbonate apatite particle is not particularly limited as long as effects of fining and/or re-aggregation suppression can be obtained, but the concentration is e.g. 0.1 to 500 mg/ml, preferably 1 to 100 mg/ml, more preferably about 1 to 10 mg/ml; or about 0.001 to 10 wt %.

(Composite Particle of miR-29a and/or miR-29b with Carbonate Apatite Particle).

In the prophylactic or therapeutic agent according to the present invention, a composite particle having the miR-29a and/or miR-29b carried on and conjugated to the carbonate apatite particle is used. The miR-29a and/or miR-29b is conjugated to the carbonate apatite particle, so that the miR-29a and/or miR-29b can be not only delivered to an inflammatory bowel disease lesion but also efficiently taken into dendritic cells. In addition, after introduced into the cells, the composite particle can cause the miR-29a and/or miR-29b to exert a desired activity, because the miR-29a and/or miR-29b can be released from the carbonate apatite particle in the cells.

In the present invention, the composite particle having the miR-29a and/or miR-29b carried on and conjugated to the carbonate apatite particle refer to a state that the miR-29a and/or miR-29b are adsorbed to and carried on the carbonate apatite particle through an ionic bond, a hydrogen bond, or the like. A method for forming the composite particle of the miR-29a and/or miR-29b with the carbonate apatite particle is not particularly limited, but examples of the method includes: a method in which composite particle is formed by allowing the miR-29a and/or miR-29b and the carbonate apatite particle to coexist in an aqueous solution; a method in which formation of carbonate apatite particle and conjugation of miRNAs and the carbonate apatite particle are simultaneously carried out by allowing the miR-29a and/or miR-29b to coexist with calcium ions, phosphate ions and hydrogencarbonate ions in an aqueous solution for preparing the carbonate apatite particle; and the like.

When formation of the carbonate apatite particle and conjugation of the miR-29a and/or miR-29b with the carbonate apatite particle are simultaneously carried out for forming the composite particle of the miR-29a and/or miR-29b with the carbonate apatite particle, e.g. 0.1 to 1000 nM, preferably 0.5 to 500 nM, more preferably 1 to 200 nM of miR-29a and/or miR-29b may be added to the aqueous solution used for preparing the carbonate apatite. Normally about 60% of the miR-29a and/or miR-29b in the aqueous solution is included in and conjugated to the carbonate apatite particle.

In the composite particle of the miR-29a and/or miR-29b with the carbonate apatite particle, a ratio of the miR-29a and/or miR-29b to the carbonate apatite particle is not particularly limited, and may be appropriately set depending on a dose the miR-29a and/or miR-29b, or the like. For example, when 2 mg of miR-29a and/or miR-29b is conjugated to the carbonate apatite particle, formation of the carbonate apatite particle and conjugation of the miR-29a and/or miR-29b with the carbonate apatite particle may be simultaneously carried out by adding 5 mg of miR-29a and/or miR-29b to 2.5 L of aqueous solution for preparing the aforementioned carbonate apatite particle.

Additionally, in the present invention, the composite particle of the miR-29a and/or miR-29b with the carbonate apatite particle is used in a state of being dispersed in a solvent suitable for in vivo administration. As described above, the carbonate apatite particle can be obtained by dissolving various ion source substances in a solvent such as water, a medium or a buffer, but a carbonate apatite particle dispersion solution obtained in such a way is not necessarily suitable for in vivo systemic administration from the viewpoints of osmotic pressure, buffer capacity, sterility, and the like. For replacing the solvent containing the dispersed carbonate apatite particle with a solvent suitable for in vivo administration (e.g. saline, etc.), typically a manipulation is required, in which the carbonate apatite particle is recovered by separating the particle from the solvent by centrifugation, filtration, gravitational sedimentation or the like, and the solvent is replaced. The carbonate apatite particle is added to a solvent suitable for in vivo administration and then subjected to the aforementioned ultrasonic vibration, so that the composite particle of the miR-29a and/or miR-29b with the carbonate apatite particle can be dispersed with appropriate particle diameters in the solvent suitable for in vivo administration. It is desirable that, after such dispersion, the composite particle is rapidly administered to a living body before aggregation. For example, the particle is desirably administered within 1 minute, preferably within 30 seconds after the ultrasonic vibration. However, when aggregation of the carbonate apatite particle is suppressed by adding a dispersant as described above, the particle can also be administered a few minutes to several tens of minutes, or one to a few days after ultrasonic vibration.

Application

Since the composite particle of the carbonate apatite particle carrying the miR-29a and/or miR-29b can effectively cure or ameliorate symptoms of inflammatory bowel disease, the prophylactic or therapeutic agent according to the present invention can be used for the purpose of treating inflammatory bowel disease. In addition, since inflammatory bowel disease gradually progress while repeating recurrence and remission in some cases, the prophylactic or therapeutic agent according to the present invention can also be used for prophylaxis and recurrence prevention of inflammatory bowel disease.

Inflammatory bowel disease is roughly classified into ulcerative colitis and Crohn's disease, and the prophylactic or therapeutic agent according to the present invention can be applied to any of these diseases.

Administration Method

The prophylactic or therapeutic agent according to the present invention is systemically administered. Local administration cannot deliver the miR-29a and/or miR-29b to dendritic cells, but systemic administration can directly deliver a part of the miRNA to a lesion, and can allow the part of the miRNA to be efficiently taken into the dendritic cells.

Specific examples of the systemic administration include intravascular (intraarterial or intravenous) administration, subcutaneous administration, intramuscular administration, intraperitoneal administration, and the like. Among them, intravascular administration and subcutaneous administration are preferable, and intravenous injection is more preferable, from the viewpoint of further improving the therapeutic effect for inflammatory bowel disease.

A dose of the prophylactic or therapeutic agent according to the present invention is appropriately determined depending on severity of inflammatory bowel disease, and sex, age, symptoms and the like of a patient. Thus, although the dose cannot be generally determined, the dose is e.g. about 1 to 100 mg/m$^2$ (body surface area) a day in terms of a mature miRNA dose of the 29a and/or miR-29b.

EXAMPLES

Hereinafter, the present invention will be explained in detail based on EXAMPLES and the like, but the present invention is not limited by EXAMPLES and the like. All the tests described below were carried out under the approval of Animal Control and Use Commission and Animal Experiment Committee in the Faculty of Medicine, Osaka University (approval number: 260033-006).

Reference Example 1: Preparation of Composite of miRNA and Carbonate Apatite

Except in Test Example 6, a composite of miRNA and carbonate apatite produced by the following method was used. First, an inorganic aqueous solution (NaHCO$_3$; 44 mM, NaH$_2$PO$_4$; 0.9 mM, CaCl$_2$; 1.8 mM, pH 7.5) was prepared. To 50 ml of this inorganic aqueous solution, 100 μg of miRNA was added, which was incubated at 37° C. for 30 minutes. Subsequently, the mixture was centrifuged at 12,000 rpm×3 minutes to obtain a pellet containing 60 μg of miRNA (composite particle having the miRNA included in carbonate apatite particle; miRNA/sCA composite). Saline (containing 0.5 wt % albumin) was added to the pellet up to 200 μL so that the pellet was dispersed, which was subjected to ultrasonic vibration (38 kHz, 80 W) for 10 minutes, and immediately used for the test. Incidentally, the obtained miRNA/sCA composite was confirmed to have an average particle diameter of 400 to 2000 nm by a dynamic light scattering particle measurement (DLS) using Zetasizer Nano ZS (Malvern Panalytical Ltd).

In the following test examples, mature miRNAs (double strand) described below were used. In the following test examples, an amount of the miRNAs used is a total amount of sense and antisense strands. Hereinafter, the carbonate apatite particle including the miR-29a is sometimes also referred to as "miRNA-29a/sCA composite" in some cases. Also, the carbonate apatite particle including other miRNA is sometimes denoted in the same description form as the above in some cases.

TABLE 1

| | | Base sequence |
|---|---|---|
| artificial miRNA (MIRTX) | Sense strand | 5'-UCU AAA CCA CCA UAU GAA ACC AGC-3' (SEQ ID NO: 5) |
| | Antisense strand | 5'-GCU GGU UUU AUA UGG UGG UUU AGA-3' (SEQ ID NO: 6) |
| miR-29a | Sense strand | 5'-UAG CAC CAU CUG AAA UCG GUU A-3' (SEQ ID NO: 1) |
| | Antisense strand | 5'-UAA CCG AUU UCA GAU GGU GCU A-3' (SEQ ID NO: 2) |
| miR-29b | Sense strand | 5'-UAG CAC CAU UUG AAA UCA GUG UU-3' (SEQ ID NO: 3) |
| | Antisense strand | 5'-AAC ACU GAU UUC AAA UGG UGC UA-3' (SEQ ID NO: 4) |
| Alexa647 tagged non-specific miRNA (Alexa647-miRNA) (Y-Alexa647, N(H)-ssH amino linker) | Sense strand | 5'-Y-N(H) -AUC CGC GCG AUA GUA CGU A-3' (SEQ ID NO: 7) |
| | Antisense strand | 5'-UAC GUA CUA UCG CGC GGA U-3' (SEQ ID NO: 8) |
| Negative control-miRNA (NC-miR) | Sense strand | 5'-UAA AUG UAC CGC GCG UGG AGA GGA A-3' (SEQ ID NO: 9) |
| | Antisense strand | 5'-UUC CUC UCC ACG CGC AGU ACA UUU A-3' (SEQ ID NO: 10) |

Reference Test Example 1

Seven-week-old BALB/c mice (CLEA Japan, Inc.) were fed with water containing 2 wt % of dextran sulfate (DSS) for 7 days to develop inflammatory enteritis, and to prepare DSS-induced mouse enteritis models. A MIRTX/sCA composite or an Alexa647-miRNA/sCA composite was intravenously administered to tails of the DSS-induced mouse enteritis models so that a dose of the miRNA was 60 µg/mouse.

In a group dosed with the MIRTX/sCA composite, mice were sacrificed 4 hours after administration, and rectums, transverse colons, cecums, and ileums were ground to recover RNAs. Subsequently, take-in levels of the MIRTX in each intestinal tract was measured by quantitative RT-PCR (n=3). Note that the MIRTX was quantitatively determined as a relative value of the MIRTX level with respect to an RNU6B level, using a RNU6B as an internal standard.

In addition, in the group dosed with the Alexa647-miRNA/sCA composite, 4 hours after administration, rectums (rectal site where the most intense inflammation was observed) were taken out from the mice to prepare frozen sections, nuclei were stained using 4',6-diamidino-2-phenylindole (DAPI), and fluoroscopically observed.

Note that, for comparison's sake, the test was conducted under the same conditions as described above except that normal mice with no DSS administration were used.

FIG. 1, (a) presents a result of measuring take-in levels of the MIRTX in each intestinal tract by administering the MIRTX/sCA composite. As a result, in the DSS-induced mouse enteritis models, the take-in levels of the MIRTX in the intestinal tracts were significantly higher than of the normal mice with no DSS, but the MIRTX take-in levels themselves were not so high.

In addition, FIG. 1, (b) presents results of microscopically observing rectums recovered after administering the Alexa647-miRNA, and nuclear-stained. Note that the scale bars are 50 µm in FIG. 1, (b). As a result, compared to the normal mouse with no DSS, the DSS-induced mouse enteritis model showed slightly increased light gray signals (fluorescence of Alexa647) indicating that the Alexa647-miRNA was taken into the rectums, but the signals were still relatively small. From the above results, it was confirmed that the take-in level of the miRNA in the intestinal tract did not reach a high level even when the miRNA/sCA composite was administered to the tail.

Test Example 1

Seven-week-old BALB/c mice (CLEA Japan, Inc.) were grouped into 6 groups presented in Table 2. Under the conditions presented in Table 2, DSS and the miRNA/sCA composite or the miRNA were administered to the mice of each group.

TABLE 2

| Group | Condition of administration |
|---|---|
| Normal group | Mice were kept without administration of DSS and a miRNA/sCA composite for 9 days, and then sacrificed. |
| DSS group | Mice were fed with water containing 2 wt % of DSS for 4, 6 or 9 days, and then sacrificed. |
| DSS + sCA-NC-miR group | Mice were fed with water containing 2 wt % of DSS for 9 days. A starting date of DSS feed was designated as day 0, an NC-miR/sCA composite was intravenously administered to tails on day 1, 2, 3 and 5 so that a dose of the miRNA was 60 µg/mouse, and then the mice were sacrificed on day 9. |
| DSS + sCA-miR-29a group | Mice were fed with water containing 2 wt % of DSS for 9 days. A starting date of DSS feed was designated as day 0, a miR-29a/sCA composite was intravenously administered to tails on day 1, 2, 3 and 5 so that a dose of the miRNA was 60 µg/mouse, and then the mice were sacrificed on day 9. |
| DSS + sCA-miR-29b group | Mice were fed with water containing 2 wt % of DSS for 9 days. A starting date of DSS feed was designated as day 0, a miR-29b/sCA composite was intravenously administered to tails on day 1, 2, 3 and 5 so that a dose of the miRNA was 60 µg/mouse, and then the mice were sacrificed on day 9. |

TABLE 2-continued

| Group | Condition of administration |
| --- | --- |
| DSS + miR-29b group | Mice were fed with water containing 2 wt % of DSS for 9 days. A starting date of DSS feed was designated as day 0, a miR-29b (naked) was intravenously administered to tails on day 1, 2, 3 and 5 so that a dose of the miRNA was 60 μg/mouse, and then the mice were sacrificed on day 9. |

The body weights of the mice were measured from the onset to the end of the test (n=5). Additionally, in the Normal group at the onset of the test, the DSS group and the DSS+sCA-miR-29b group on day 4 and day 6 from the onset of the test, the mice were sacrificed, and large intestine mucosas were recovered and ground to recover RNAs. Subsequently, miR-29b-3p expression levels were measured by quantitative RT-PCR (n=3). Incidentally, the miR-29b-3p expression levels were quantitatively determined as relative values of the miR-29b expression levels with respect to RNU6B levels, using RNU6B as an internal standard.

In addition, large intestines were recovered from mice sacrificed on day 9. In the recovered large intestines, lengths of the large intestines were measured, and the rectal sites where the most intense inflammation was observed were stained with Hematoxylin-Eosin (HE), and states of inflammation were microscopically observed (n=5). In addition, inflammation severities of the rectal sites where the most intense inflammation was observed were scored for mucosal damages, submucous tissue damages, and muscle layer damages in accordance with the following criteria, and a total value of these scores was calculated as a histological inflammation score (n=5).

Figure 2:
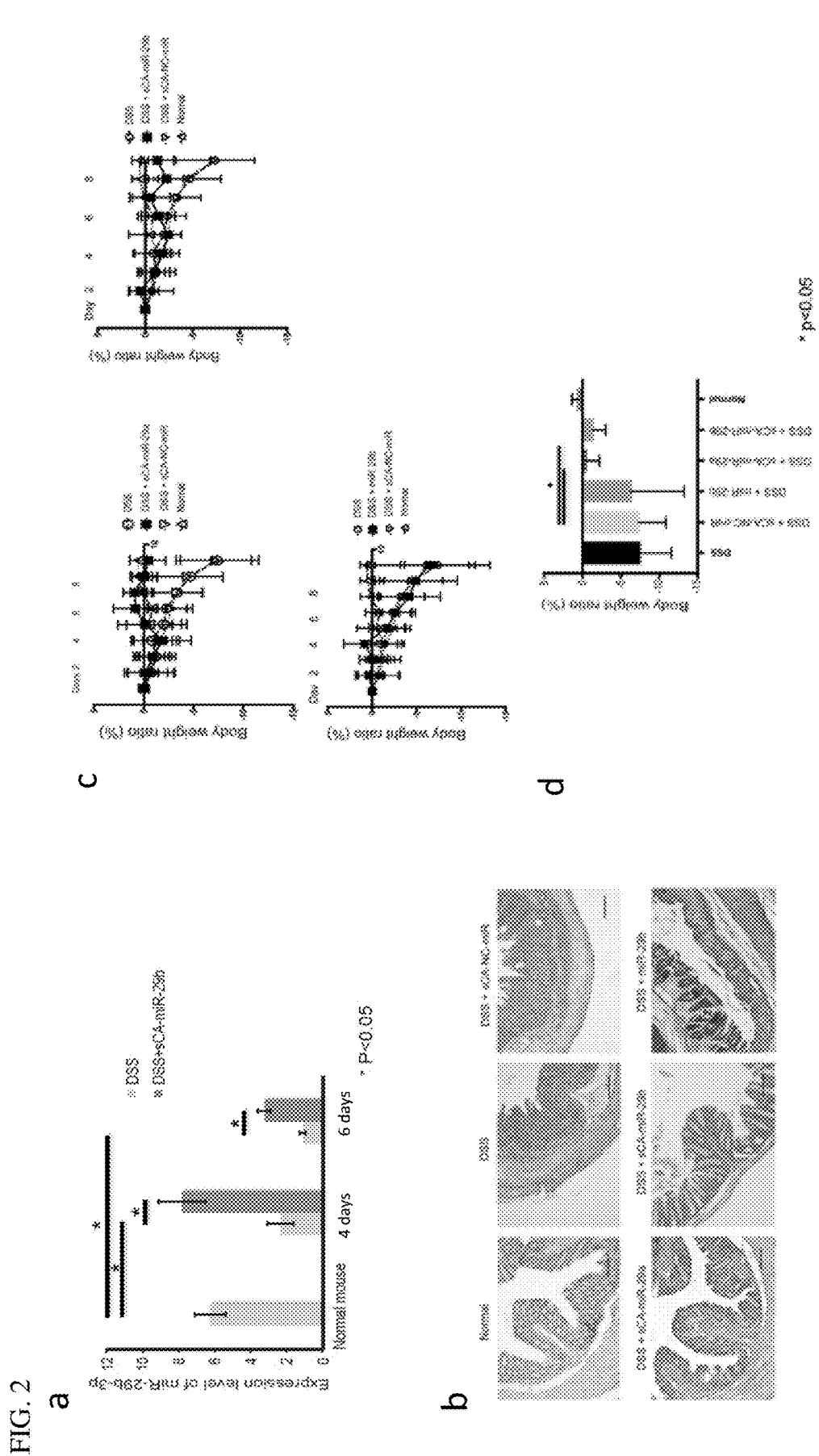
FIG. 2. (a) is a diagram illustrating a result of Test Example 1, which presents a result of measuring miR-29b-3p expression levels in large intestine mucosas taken out from mice to which DSS and a miR-29b/sCA composite have been intravenously administered. (b) is a diagram illustrating a result of Test Example 1, which presents results of microscopically observing rectums resected from mice to which DSS and various miRNA/sCA composites have been intravenously administered, and stained with HE. (c) is a diagram illustrating a result of Test Example 1, which presents results of time-sequentially measuring body weights of the mice. (d) is a diagram illustrating a result of Test Example 1, which presents a result of time-sequentially measuring the body weights of the mice 7 days after onset of the test.

<Mucosal Damage>
0: normal
1: 3-10 intraepithelial lymphocytes (IEL)/high power field (HPF) and focal damage
2: 10 IEL/HPF and rare crypt abscesses
3: 10 IEL/HPF, multiple crypt abscesses and erosion/ulceration
<Submucous Tissue Damage>
0: normal or widely scattered leukocytes
1: focal aggregates of leukocytes
2: diffuse leukocyte infiltration with expansion of submucosa
3: diffuse leukocyte infiltration
<Muscle Layer Damage>
0: normal or widely scattered leukocytes
1: widely scattered leukocyte aggregates between muscle layers
2: leukocyte infiltration with focal effacement of the muscularis
3: extensive leukocyte infiltration with transmural effacement of the muscularis FIG. 2, (a) presents a result of measuring the miR-29b-3p expression levels in the large intestine mucosa for the DSS group and the DSS+sCA-miR-29b group. As a result, it was confirmed that the miR-29b expression level in the DSS group was decreased compared to the Normal group, but decrease in the miR-29b expression level in the DSS+sCA-miR-29b group could be significantly suppressed compared to the DSS group.

FIG. 2, (b) presents results of observing rectums stained with HE. As a result, in the DSS group, the DSS+sCA-NC-miR group, and the DSS+miR-29b group, it was confirmed that the rectal mucosal structure was destroyed and numerous inflammatory cells infiltrated the mucosa. On the other hand, in the DSS+sCA-miR-29a group and the DSS+sCA-miR-29b group, the colonic mucosal structure was almost normally maintained, and also infiltration of inflammatory cells was hardly observed.

FIG. 2, (c) presents results of time-sequentially measuring body weights of the mice, and FIG. 2, (d) presents a result of measuring the body weights of the mice 7 days after the onset of the test. In addition, FIG. 3, (a) presents a result of measuring lengths of large intestines, and FIG. 3, (b) presents a result of a histological inflammation scoring. As a result, in the DSS+sCA-miR-29a group and the DSS+sCA-miR-29b group, suppression of mouse body weight loss, suppression of large intestine shortening, and lowering of the histological inflammation score were significantly observed compared to the DSS group, the DSS+sCA-NC-miR group, and the DSS+miR-29b group.

The above results demonstrated that intravenous administration of the miR-29a/sCA composite and miR-29b/sCA composite could effectively improve inflammatory bowel disease though the direct take-in levels of the miRNA in the intestinal tracts is low (result of Reference Test Example 1 described above).

Figure 3:
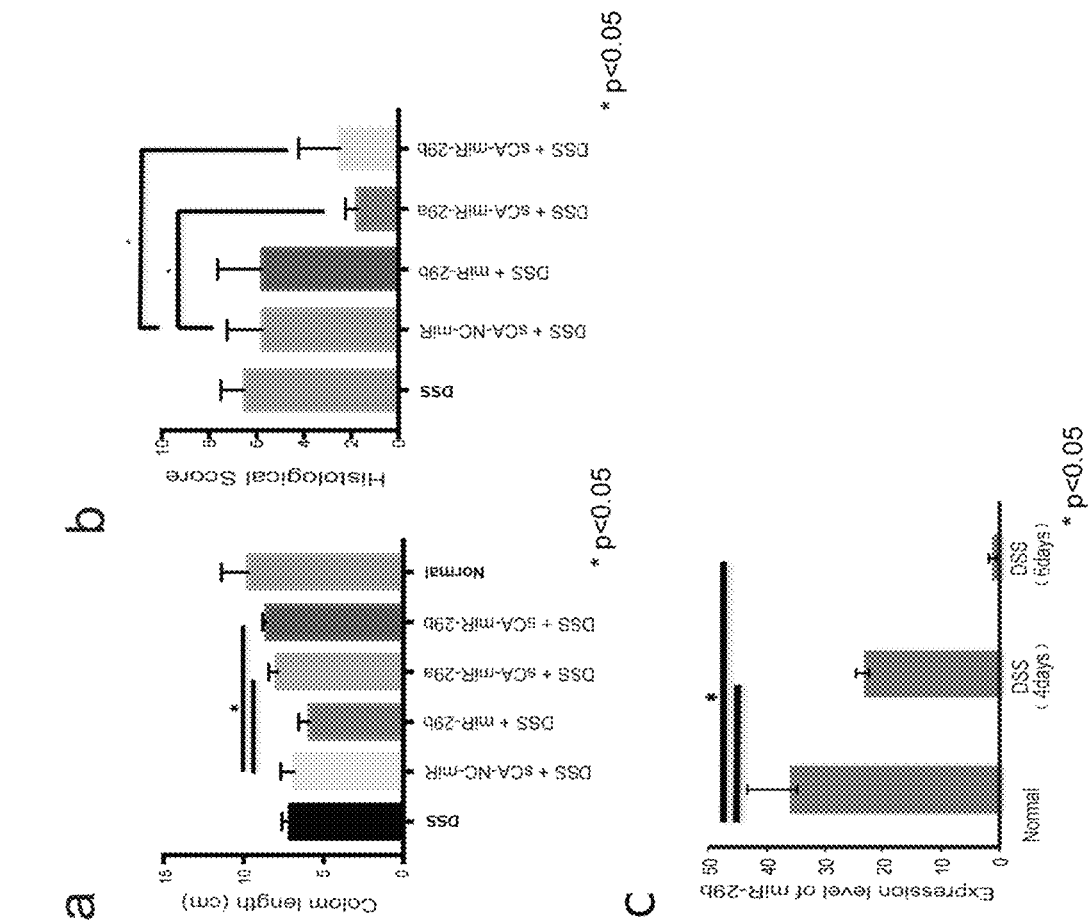
FIG. 3. (a) is a diagram illustrating a result of Test Example 1, which presents a result of measuring lengths of large intestines 7 days after onset of the test in mice to which DSS and various miRNA/sCA composites were intravenously administered. (b) is a diagram illustrating a result of Test Example 1, which presents a result of scoring colonic and rectal inflammation severities of the mice 7 days after onset of the test. (c) is a diagram illustrating a result of Test Example 1, which presents a result of measuring miR-29b expression levels in large intestines in a normal group at onset of the test, and DSS groups 4 and 6 days after onset of the test.

FIG. 3, (c) presents a result of measuring the miR-29b expression levels in large intestines in the normal group at the onset of the test, and the DSS groups 4 and 6 days after the onset of the test. This result demonstrated that the miR-29b expression levels in the large intestines were decreased in the inflammatory bowel disease-developing mice.

Reference Test Example 2

Seven-week-old BALB/c mice (CLEA Japan, Inc.) were fed with water containing 2 wt % of DSS for 7 days to develop inflammatory enteritis, and to prepare DSS-induced mouse enteritis models. The Alexa647-miRNA/sCA composite was intravenously administered to tails of the DSS-induced mouse enteritis models so that a dose of the miRNA was 60 μg/mouse. Four hours after administration of the Alexa647-miRNA/sCA composite, large intestines were taken out from the mice to prepare frozen sections of rectum sites where the most intense inflammation was observed, immunostained using an anti-CD11c antibody and DAPI (CD11c is light gray), and fluoroscopically and confocal-microscopically observed. In addition, for comparison's sake, the test was conducted under the same conditions as described above except that normal mice with no DSS administration were used.

Figure 4:
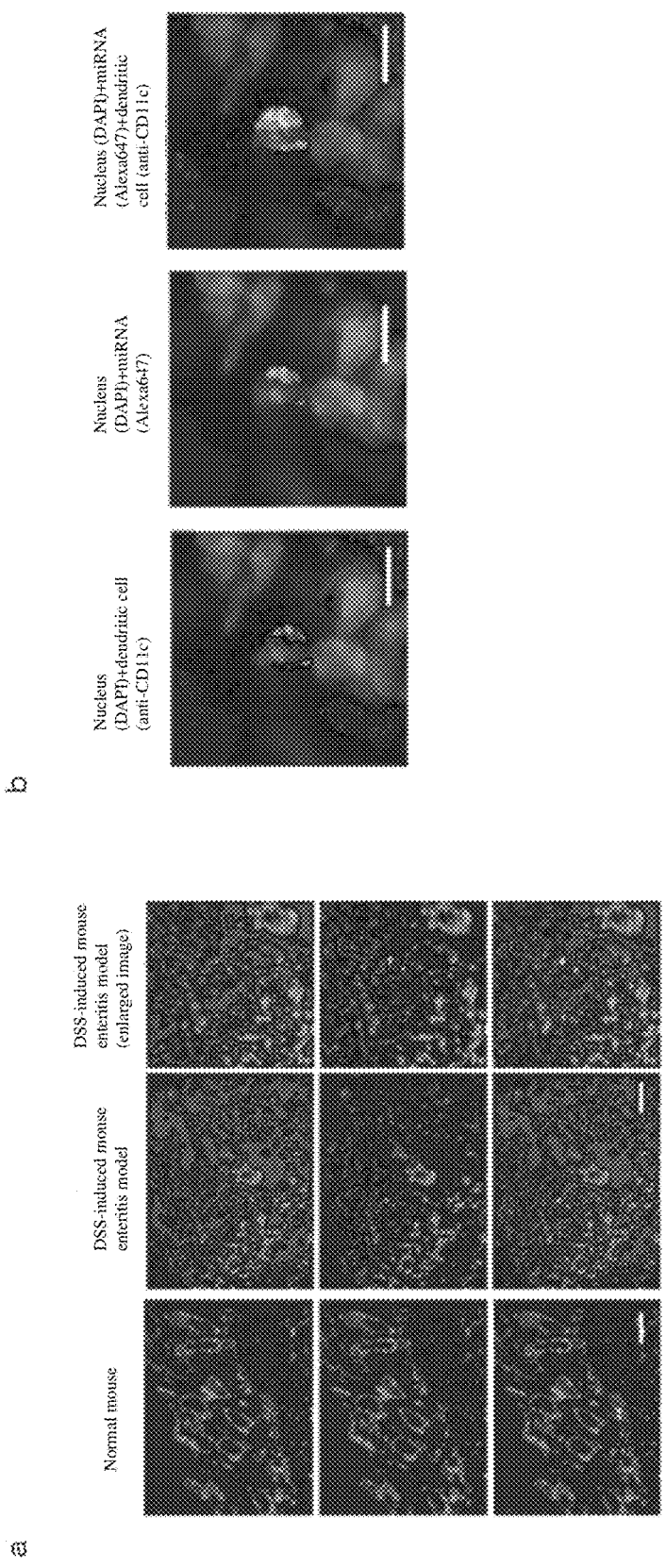
FIG. 4. (a) is a diagram illustrating a result of Reference Test Example 2, which presents images indicating results of fluoroscopically observing rectums immunostained with an anti-CD11c antibody and DAPI after intravenously administering the Alexa647-miRNA/sCA composite to DSS-induced mouse enteritis models. (b) is a diagram illustrating a result of Reference Test Example 2, which presents images indicating results of confocal-microscopically observing the immunostained rectums.

FIG. 4, (a) presents results of fluoroscopically observing immunostained frozen sections, and FIG. 4, (b) presents results of confocal-microscopically observing sections using DSS-induced mouse enteritis models. Note that the scale bars in FIG. 4, (a) are 50 μm, and the scale bars in FIG. 4, (b) are 5 μm. In FIG. 4, (a), the upper images present results of observing dark gray signals emitted by the Alexa647-miRNA and black signals emitted by DAPI, the middle images present results of observing light gray signals emitted by the anti-CD11c antibody and the black signals emitted by DAPI, and the lower images are images obtained by merging the upper images and the middle images. Color development resulting from the anti-CD11c antibody indicates the presence of the dendritic cells.

From FIG. 4, (a), it was confirmed that a distribution of the dark gray signals emitted by the Alexa647-miRNA and a distribution of the light gray signals emitted by the anti-CD11c antibody were coincident with each other. Furthermore, from FIG. 4, (b), it was found that the light gray signals emitted by the anti-CD11c antibody were present on cell surfaces, and the dark gray signals emitted by the Alexa647-miRNA were filled in cytoplasm. The results described above demonstrated that once the siRNA/sCA composite was intravenously administered, the siRNA/sCA composite was taken into the dendritic cells and the dendritic cells were active in the intestinal tract.

Test Example 2

Seven-week-old BALB/c mice (CLEA Japan, Inc.) were fed with water containing 2 wt % of DSS for 7 days to develop inflammatory enteritis, and to prepare DSS-induced mouse enteritis models. On day 1, 2, and 3, an sCA-miR-29a/sCA composite or an sCA-miR-29b/sCA composite was intravenously administered to tails of the DSS-induced mouse enteritis models so that a dose of the miRNA was 60 μg/mouse, and on day 4, large intestines were taken out from the mice. Lamina propria cells were extracted from large intestine mucosas, from which CD11c-positive cells were separated using the anti-CD11c antibody and autoMACS Pro Separator. RNAs were extracted from the obtained CD11c-positive cells. Subsequently, expression levels of various cytokines (IL12 p40, IL23 p19, IL-6, and TGF-β) were measured by quantitative RT-PCR (n=3). Incidentally, using β-actin as an internal standard, the expression level of each cytokine was quantitatively determined as a relative value of each cytokine expression level with respect to the β-actin level.

In addition, for comparison's sake, each cytokine expression level was measured in the same manner as described above also for normal mice with no DSS and no miRNA/sCA composite administration (Normal), and for DSS-induced mouse enteritis models dosed with DSS alone but no miRNA/sCA composite (DSS).

Figure 5:
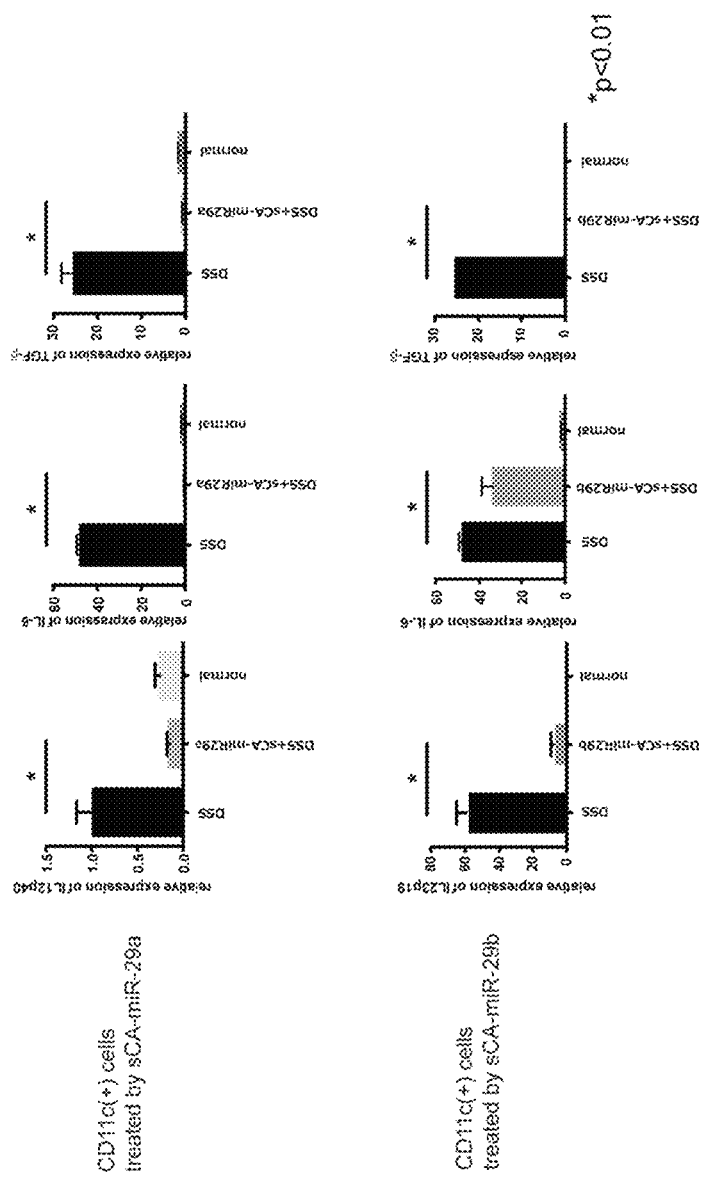
FIG. 5 is a diagram illustrating results of measuring expression levels of messenger RNAs of various cytokines (IL12 p40, IL23 p19, IL-6, and TGF-β) in dendritic cells isolated from mucosas of large intestines recovered after intravenously administrating an sCA-miR-29a/sCA composite or an sCA-miR-29b/sCA composite to DSS-induced mouse enteritis models, in Test Example 2.

FIG. 5 presents the obtained results. As a result, it was found that expression levels of IL12 p40, IL23 p19, IL-6, and TGF-β were significantly decreased by intravenously administering the sCA-miR-29a/sCA composite or sCA-miR-29b/sCA composite to the DSS-induced mouse enteritis models. The IL-6 and the TGF-β are cytokines which are known to be involved in differentiation of naive T cells into Th-17 cells, and the IL12 p40 and the IL23 p19 are cytokines which are known to activate and lead the Th-17 cells to pathogenic Th-17 cells. That means, it is presumed that the miR-29a or miR-29b accumulates in dendritic cells by intravenously administering the sCA-miR-29a/sCA composite or the sCA-miR-29b/sCA composite, so that down regulation of the IL-6 and TGF-β suppresses differentiation of the naive T cells into the Th-17 cells, and downregulation of the IL12 p40 and the IL23 p19 prevents the Th-17 cells from being activated to become pathogenic Th-17 cells.

Test Example 3

Seven-week-old BALB/c mice (CLEA Japan, Inc.) were grouped into 4 groups presented in Table 3. Under the conditions presented in Table 3, DSS and the miRNA/sCA composite were administered to the mice in each group.

TABLE 3

| Group | Condition of administration |
| --- | --- |
| Normal group | Mice were kept without administration of DSS and a miRNA/sCA composite for 4 days, and then sacrificed. |

TABLE 3-continued

| Group | Condition of administration |
| --- | --- |
| sCA-NC-miR group | Mice were fed with water containing 2 wt % of DSS for 4 days. A starting date of DSS feed was designated as day 0, an NC-miR/sCA composite was intravenously administered to tails so that a dose of the miRNA was 60 μg/mouse on day 1, 2 and 3, and then the mice were sacrificed on day 4. |
| sCA-miR-29a group | Mice were fed with water containing 2 wt % of DSS for 4 days. A starting date of DSS feed was designated as day 0, a miR-29a/sCA composite was intravenously administered to tails so that a dose of the miRNA was 60 μg/mouse on day 1, 2 and 3, and then the mice were sacrificed on day 4. |
| sCA-miR-29b group | Mice were fed with water containing 2 wt % of DSS for 4 days. A starting date of DSS feed was designated as day 0, a miR-29b/sCA composite was intravenously administered to tails so that a dose of the miRNA was 60 μg/mouse on day 1, 2 and 3, and then the mice were sacrificed on day 4. |

Large intestines were recovered from the sacrificed mice. RNAs were extracted from the recovered large intestines, and an mRNA library was prepared using TruSeq stranded mRNA sample prep kit (Illumina, Inc., San Diego, Calif.) in accordance with a manufacturer's instruction. The sequences were determined using Illumina HiSeq 2500 platform (75-base single-end mode). Base calling was carried out using Illumina Casava 1.8.2 software. The determined sequences were mapped on a mouse reference genome sequence (mm10) using TopHat v2.0.13 with Bowtie2 ver. 2.2.3 and SAMtools ver. 0.1.19 TopHat v2.0.13 in combination. One million read sequences were mapped, and gene expression levels normalized under a condition that a length of a transcription product (fragment) was 1 kilobase were calculated using Cuffnorm version 2.2.1.

Subsequently, pathway analysis was carried out using QIAGEN's Ingenuity Pathway Analysis (IPA, QIAGENRedwood City, www.qiagen.com/ingenuity) (cut-off value was set to P<0.05 for each gene).

Figure 6:
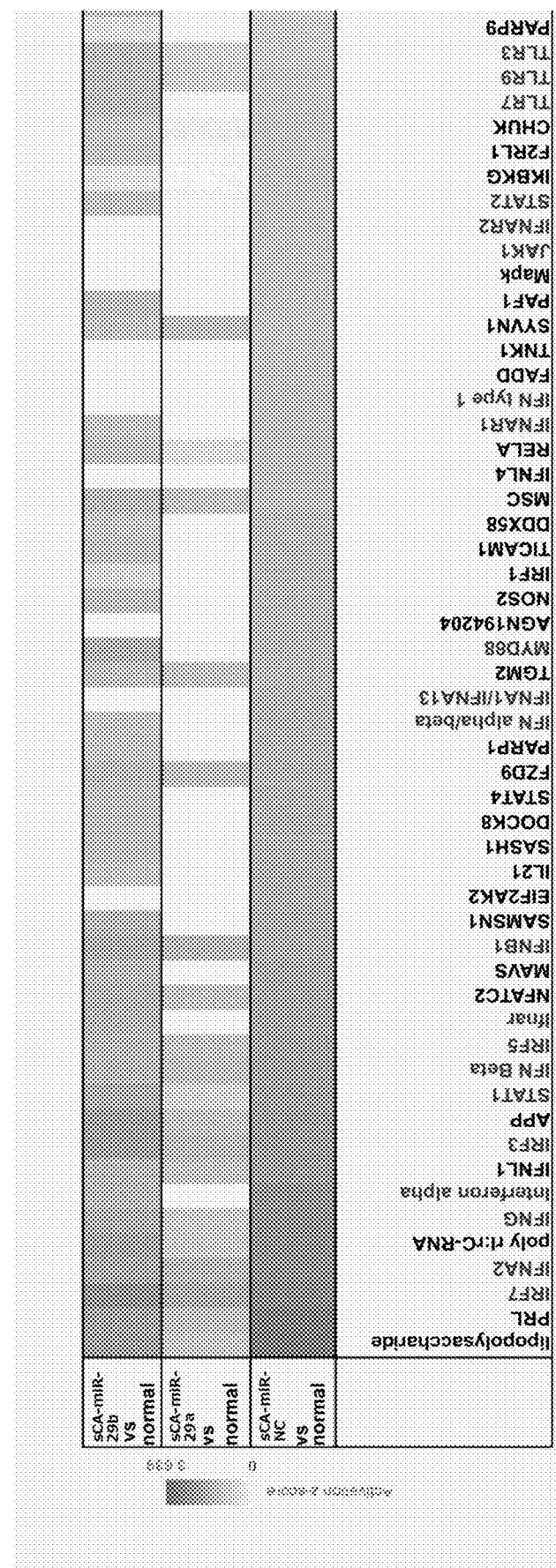
FIG. 6 is a diagram illustrating results of analyzing gene expression levels by IPA using large intestines resected from mice to which DSS and various miRNA/sCA composites were intravenously administered in Test Example 3.

FIG. 6 presents results of analyzing gene expression levels by IPA. In FIG. 6, in comparing the Normal group with the sCA-NC-miR groups, molecules showing activated molecules i.e. molecules activated by DSS administration in the sCA-NC-miR group were picked up. FIG. 6 indicates that the deeper the color is, the higher the activation level (expression level) is. In addition, underlined molecules in FIG. 6 have identified as lots of IFN pathway-related molecules. As a result, in the sCA-miR-29a group and the sCA-miR-29b group, there was a tendency that Z scores (activation levels) of the activated molecules in the sCA-NC-miR group were decreased.

Figure 7:
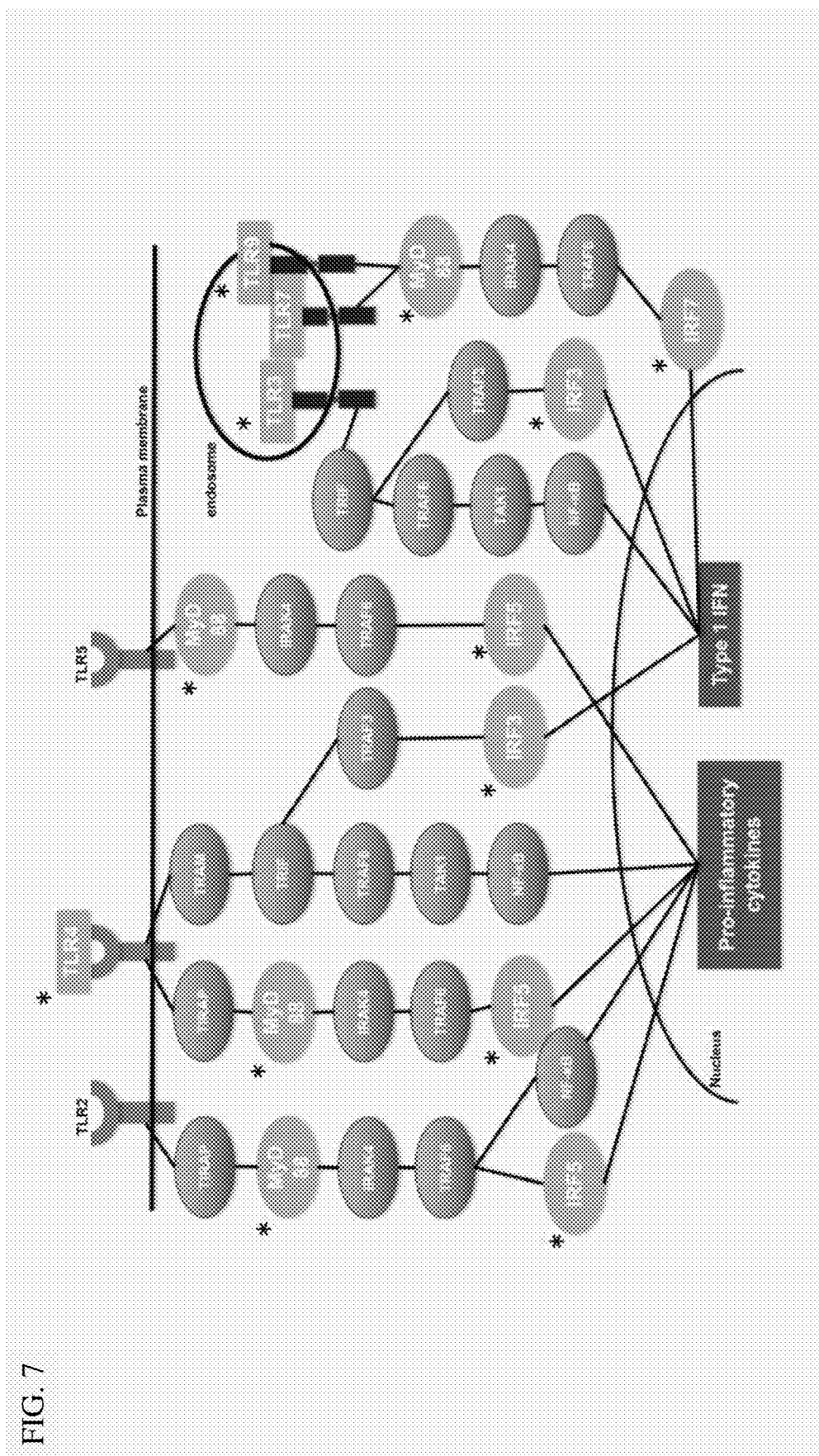
FIG. 7 is an intracellular signaling pathway map related to production of IFN and inflammatory cytokines from a Toll-like receptor (TLR), in which molecules marked with * are molecules which have been recognized to be activated by intravenous administration of DSS.
Figure 8:
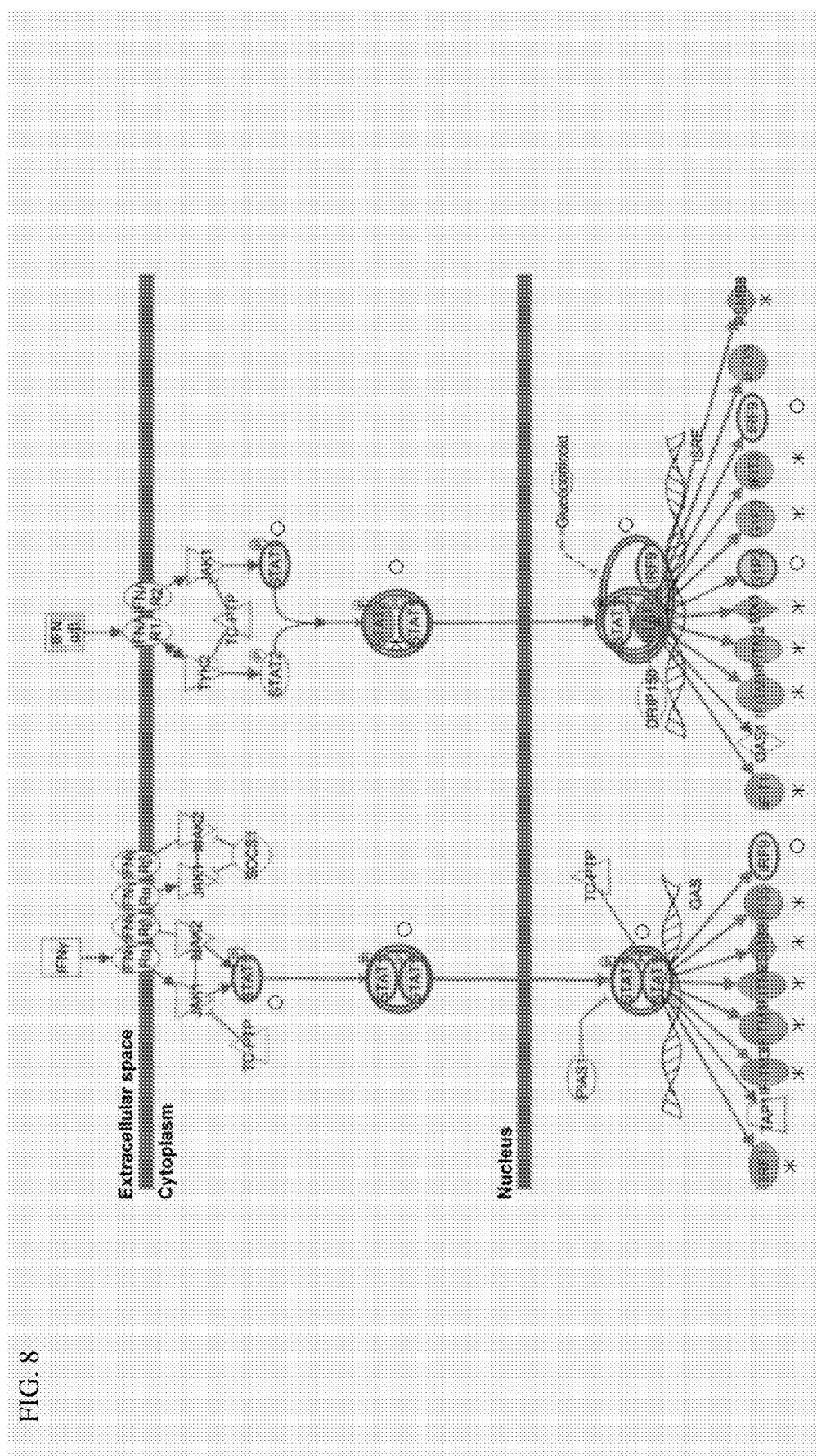
FIG. 8 is an IFN signaling pathway, in which molecules marked with * are molecules whose gene activation was predicted by IPA, and molecules marked with circle are molecules whose up-regulation has been confirmed by an mRNA array.

In addition, FIG. 7 presents an intracellular signaling pathway map related to production of IFN and inflammatory cytokines from a Toll-like receptor (TLR). In FIG. 7, for the molecules marked with *, activation by DSS administration was observed. Furthermore, FIG. 8 presents a known IFN signaling pathway. In FIG. 8, the molecules marked with * are molecules for which the activation of genes predicted to be activated by IPA has been predicted, and molecules marked with circles are molecules for which up regulation has been confirmed by an mRNA array.

Test Example 4

Seven-week-old BALB/c mice (CLEA Japan, Inc.) were grouped into 4 groups presented in Table 4 (n=3 in each group). DSS and the miRNA/sCA composite were administered to the mice in each group under the conditions presented in Table 4.

TABLE 4

| Group | Condition of administration |
| --- | --- |
| Normal group | Mice were kept without administration of DSS and a miRNA/sCA composite for 9 days, and then sacrificed. |
| DSS group | Mice were fed with water containing 2 wt % of DSS for 7 days, then kept for 9 days, and sacrificed. (no miRNA/sCA composite administration) |
| DSS + sCA-NC-miR group | Mice were fed with water containing 2 wt % of DSS for 7 days. A starting date of DSS feed was designated as day 0, an NC-miR/sCA composite was subcutaneously administered to the mice so that a dose of the miRNA was 60 μg/mouse on day 1, 2, 3 and 5, and then the mice were sacrificed on day 9. |
| DSS + sCA-miR-29b group | Mice were fed with water containing 2 wt % of DSS for 7 days. A starting date of DSS feed was designated as day 0, a miR-29b/sCA composite was subcutaneously administered to the mice so that a dose of the miRNA was 60 μg/mouse on day 1, 2, 3 and 5, and then the mice were sacrificed on day 9. |

Body weights of the mice were measured from the onset to the end of the test. In addition, large intestines were recovered from the mice, lengths of the large intestines were measured, and the rectal sites where the most intense inflammation was observed were stained with Hematoxylin-Eosin (HE), and states of inflammation were microscopically observed. Furthermore, inflammation severities of the rectal sites where the most intense inflammation was observed were scored in the same manner as in Test Example 1 to determine a histological inflammation score.

Figure 9:
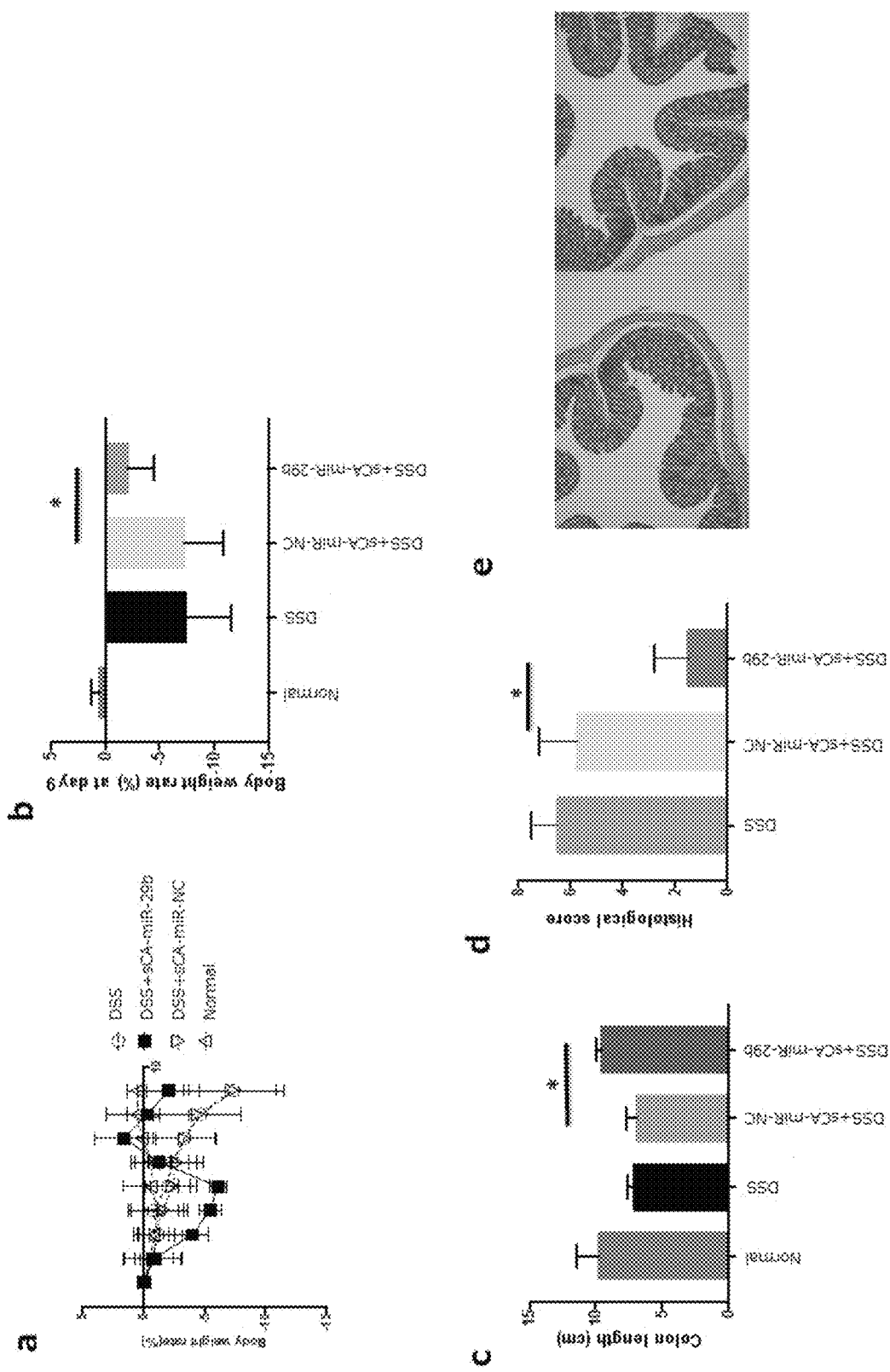
FIG. 9. (a) is a diagram illustrating a result of Test Example 4, which presents a result of time-sequentially measuring body weights of mice to which DSS and various miRNA/sCA composites were subcutaneously administered. (b) is a diagram illustrating a result of Test Example 4, which presents a result of measuring body weights of the mice at the end of the test. (c) is a diagram illustrating a result of Test Example 4, which presents a result of measuring lengths of large intestines of the mice. (d) is a diagram illustrating a result of Test Example 4, which presents a result of scoring rectal inflammation severities of the mice. (e) is a diagram illustrating a result of Test Example 4, which presents a result of microscopically observing rectums resected from a DSS+sCA-miR-29b group, and stained with HE.

FIG. 9, (a) presents a result of time-sequentially measuring body weights of the mice, and FIG. 9, (b) presents a result of measuring the body weights of the mice at the end of the test (day 9 from the onset of the miRNA/sCA composite administration). In addition, FIG. 9, (c) presents a result of measuring lengths of large intestines, and FIG. 9, (d) presents a result of the histological inflammation score. As a result, in the DSS+sCA-miR-29b group, suppression of mouse body weight loss, suppression of large intestine shortening, and lowering of the histological inflammation score were significantly observed compared to the DSS group and the DSS+sCA-NC-miR group.

In addition, FIG. 9, (e) presents a result of observing a rectum stained with HE for the DSS+sCA-miR-29b group. As shown in FIG. 9, (e), in the DSS+sCA-miR-29b group, the colonic mucosal structure was almost normally maintained, and also infiltration of inflammatory cells was hardly observed.

From the above results, it was confirmed that the miR-29b/sCA composite could effectively improve inflammatory bowel disease not only by intravenous administration but also by subcutaneous administration. That means, these results strongly suggested that the miR-29a/sCA composite and the miR-29b/sCA composite could effectively treat inflammatory bowel disease by systemic administration.

Test Example 5

Seven-week-old BALB/c mice (CLEA Japan, Inc.) were fed with water containing 2 wt % of DSS for 7 days to develop inflammatory enteritis, and to prepare DSS-induced mouse enteritis models. An Alexa647-conjugated miR-29b/sCA composite was subcutaneously administered to the DSS-induced mouse enteritis models so that a dose of the miRNA was 60 μg/mouse.

Four hours after administration of the composite, large intestines were taken out from the mice to prepare frozen sections of rectum sites where the most intense inflammation was observed, which were immunostained using an anti-CD11c antibody, an anti-Ly-6G antibody, an anti-F4/80 antibody, an anti-CD4 antibody, an anti-CD45R antibody, and DAPI, and fluoroscopically observed.

Figure 10:
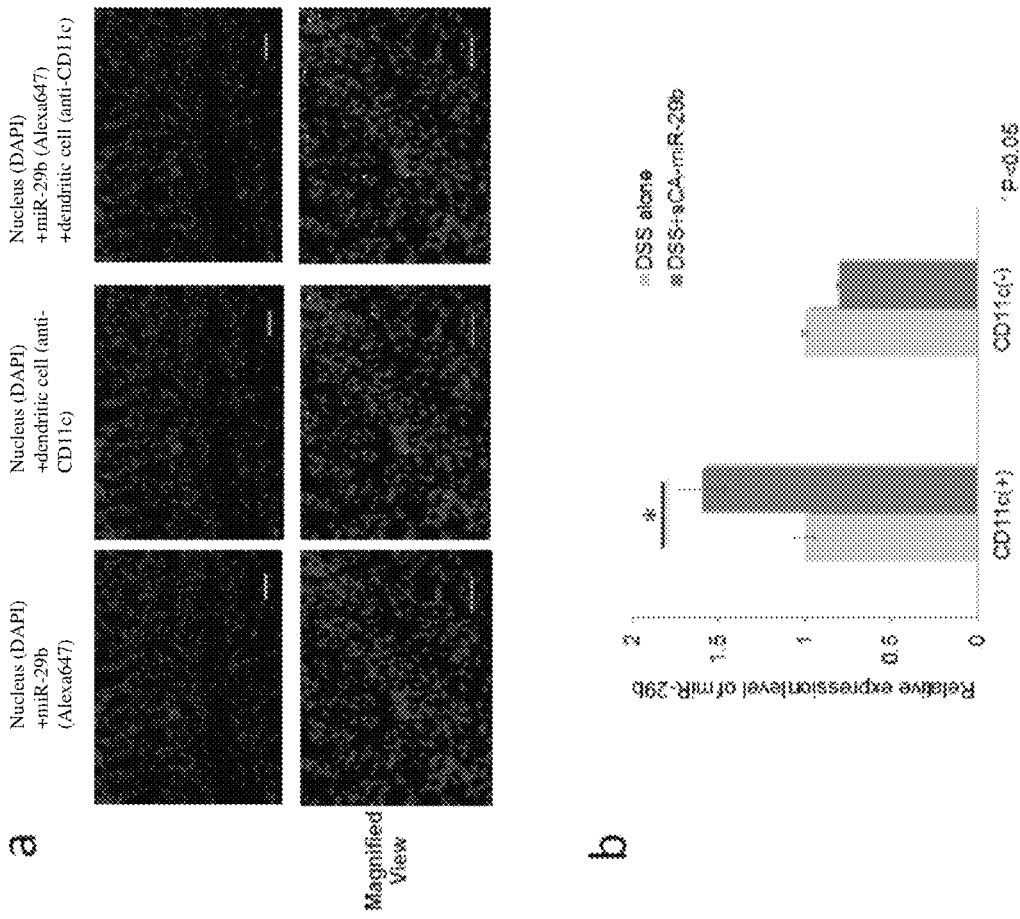
FIG. 10. (a) is a diagram illustrating a result of Test Example 5, which presents images indicating results of fluoroscopically observing rectums immunostained with an anti-CD11c antibody and DAPI after subcutaneously administering an Alexa647-miR-29b/sCA composite to DSS-induced mouse enteritis models. (b) is a diagram illustrating a result of Test Example 5, which presents a result of measuring miR-29b levels in CD11c-positive cells and CD11c-negative cells separated from large intestines of the mice.

FIG. 10, (a) presents results of fluoroscopically observing frozen sections obtained by immunostaining nuclei and CD11c' dendritic cells with the anti-CD11c antibody (light gray) and DAPI (black). From FIG. 10, (a), it was confirmed that a distribution of the dark gray signals emitted by the Alexa647-miRNA and a distribution of the light gray signals emitted by the anti-CD11c antibody were coincident with each other. That means, from this result, it was confirmed that when subcutaneously administering the Alexa647-conjugated miR-29b/sCA composite, the miRNA was efficiently taken into the dendritic cells and localized on an inflamed intestinal tract.

In addition, lamina propria cells were extracted from the large intestines taken as described above, and CD11c cells were separated into CD11c-positive cells and CD11c-negative cells using the anti-CD11c antibody and autoMACS Pro Separator. RNAs were recovered from the obtained CD11c-positive cells and CD11c-negative cells respectively. Subsequently, miR-29b levels were measured by quantitative RT-PCR. The miR-29b level was quantitatively determined as a relative value with respect to 1 of the miR-29b expression level with no composite administration. FIG. 10, (b) presents the result. As a result, in relation to the CD11c-positive cells, it was confirmed that the miR-29b level increased in the group dosed with the Alexa647-miRNA (DSS+sCA-miR-29b) compared to the group dosed with DSS alone (DSS alone). The increase in the miR-29b level may be caused by the foreign miR-29b (i.e. Alexa 647-conjugated miR-29b) taken into the CD11c-positive cells. From the above results, it was demonstrated that localization patterns of the subcutaneously administered Alexa 647-conjugated miR-29b and the CD11c positive cells were coincident with each other, and it was confirmed that the subcutaneously administered Alexa 647-conjugated miR-29b was taken into the dendritic cells and localized on the inflamed intestinal tract.

Figure 11:
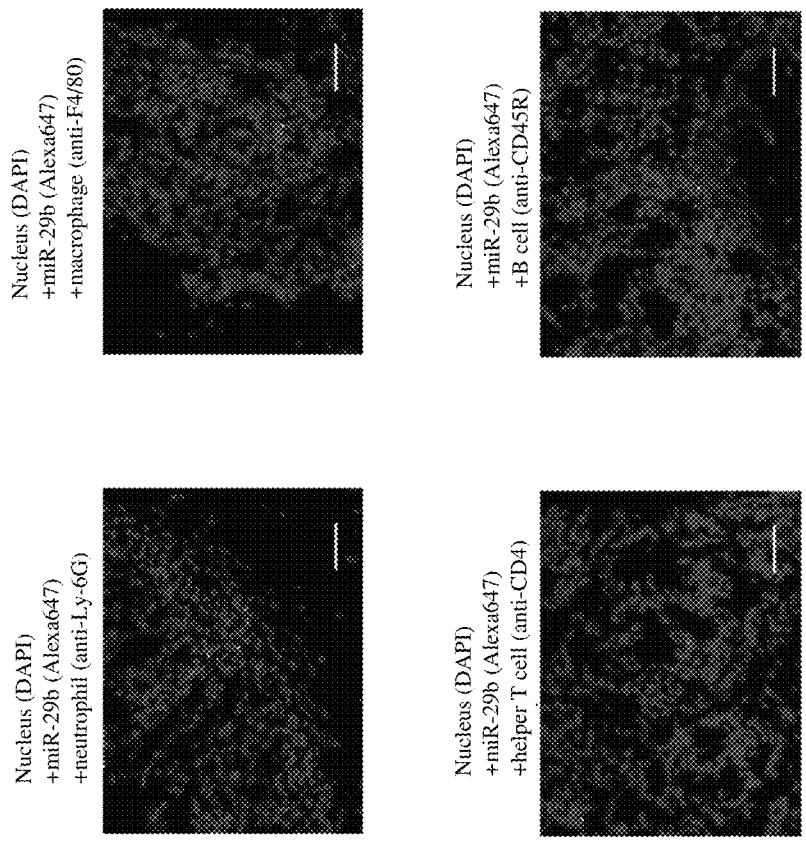
FIG. 11 presents images indicating results of fluoroscopically observing rectums immunostained with the anti-Ly-6G antibody, the anti-F4/80 antibody, the anti-CD4 antibody, the anti-CD45R antibody, and DAPI after subcutaneously administering the Alexa647-miR-29b/sCA composite to the DSS-induced mouse enteritis models in Test Example 5.

In addition, FIG. 11 presents a result of immunostaining a nucleus and a Ly-6G$^+$ neutrophil with the anti-Ly-6G antibody (light gray) and DAPI (black), a result of immunostaining a nucleus and a F4/80$^+$ macrophage with the anti-F4/80 antibody (light gray) and DAPI (black), a result of immunostaining a nucleus and a CD4$^+$ helper T cell with the anti-CD4 antibody (light gray) and DAPI (black), and a result of immunostaining a nucleus and a CD45R$^+$ B cell with the anti-CD45R antibody (light gray) and DAPI (black). As a result, it was confirmed that the dark gray color exhibited by the Alexa 647-conjugated miR-29b did not overlap the light gray color exhibited by each of the immunocytes, and the subcutaneously administered Alexa 647-conjugated miR-29b was not taken into immunocytes other than the dendritic cells.

Test Example 6

(1) Preparation of miR-29b/sCA Composite

First, an inorganic aqueous solution (NaHCO$_3$; 44 mM, NaH$_2$PO$_4$; 0.9 mM, CaCl$_2$; 1.8 mM, pH 7.5) was prepared. To 50 ml of this inorganic aqueous solution, 100 μg of miR-29b was added, which was incubated at 37° C. for 30 minutes. Subsequently, the mixture was centrifuged at 12,000 rpm×3 minutes to obtain a pellet containing 60 μg of miRNA (composite particle having the miRNA included in carbonate apatite particle; miRNA/sCA composite). Saline (containing 0.5 wt % albumin) was added to the pellet up to 200 μL so as to disperse the pellet, which was subjected to ultrasonic vibration (38 kHz, 80 W), then separated into particles having diameters of larger than 50 nm and about 3000 nm or smaller (hereinafter, miR-29b/sCA composite (>50 nm)) and particles having diameters of 10 nm or larger and 50 nm or smaller (hereinafter, miR-29b/sCA composite (≤50 nm)), and immediately used for the test.

(2) Test Method

Eight-week-old BALB/cAJc1 mice (female) were grouped into three groups (two mice per group) presented in Table 5. Under the conditions presented in Table 5, DSS and the miR-29b/sCA composite were administered to the mice in each group.

TABLE 5

| Group | Condition of administration |
| --- | --- |
| DSS group | Mice were fed with water containing 2 wt % of DSS for 9 days. A starting date of DSS feed was designated as day 0, saline was intravenously administered to the mice on day 1, 2, 3 and 5, and then the mice were sacrificed on day 9. (no miR-29b/sCA composite administration) |
| DSS + sCA (>50 nm)-miR-29b group | Mice were fed with water containing 2 wt % of DSS for 7 days. A starting date of DSS feed was designated as day 0, a miR-29b/sCA composite (>50 nm) was intravenously administered to the mice so that a dose of the miRNA was 200 μg/mouse on day 1, 2, 3 and 5, and then the mice were sacrificed on day 9. |
| DSS + sCA (≤50 nm)-miR-29b group | Mice were fed with water containing 2 wt % of DSS for 7 days. A starting date of DSS feed was designated as day 0, a miR-29b/sCA composite (≤50 nm) was intravenously administered to the mice so that a dose of the miRNA was 200 μg/mouse on day 1, 2, 3 and 5, and then the mice were sacrificed on day 9. |

Large intestines were recovered from the sacrificed mice, stained with Hematoxylin-Eosin (HE), and inflammatory states were microscopically observed to histologically evaluate inflammation severities. The inflammation severities were scored on a scale of 0 to 3 points according to the following criteria, for three items "damage of lamina propria", "damage of submucosa" and "damage of muscle layer", with a total score of 9 points. In addition, for evaluating the inflammation severities, the total length of the recovered large intestine was equally divided into 10 parts, and evaluation results of 10 visual fields were averaged to score the severities.

<Criteria for Damage of Lamina Propria>
0 point: Normal
1 point: 3 to 10 intraepithelial lymphocytes (IEL) and local mucosal damages are observed per one high power field (HPF).
2 point: Equal to or more than 10 IELs and a little crypt abscess are observed per HPF.
3 point: Equal to or more than 10 IELs, scattered crypt abscesses, and a little erosion and ulcer are observed per HPF.

<Criteria for Damage of Submucosa>
0 point: Normal; or Slight neutrophil infiltration is observed.
1 point: Local neutrophil infiltration is observed.
2 point: Diffuse neutrophil infiltration associated with enlarged submucosa is observed.
3 point: Neutrophil infiltration is observed throughout the submucosa.

<Criteria for Damage of Muscle Layer>
0 point: Normal; or some neutrophils are observed on a part of muscle layers.
1 point: Although the muscle layers are preserved, diffuse neutrophil infiltration is observed between muscle layers.
2 point: Arrange of the muscle layers is disturbed due to neutrophil infiltration.
3 point: Arrange of the muscle layers is transmurally disturbed due to a wide range of neutrophil infiltration.

(3) Test Results

Figure 12:
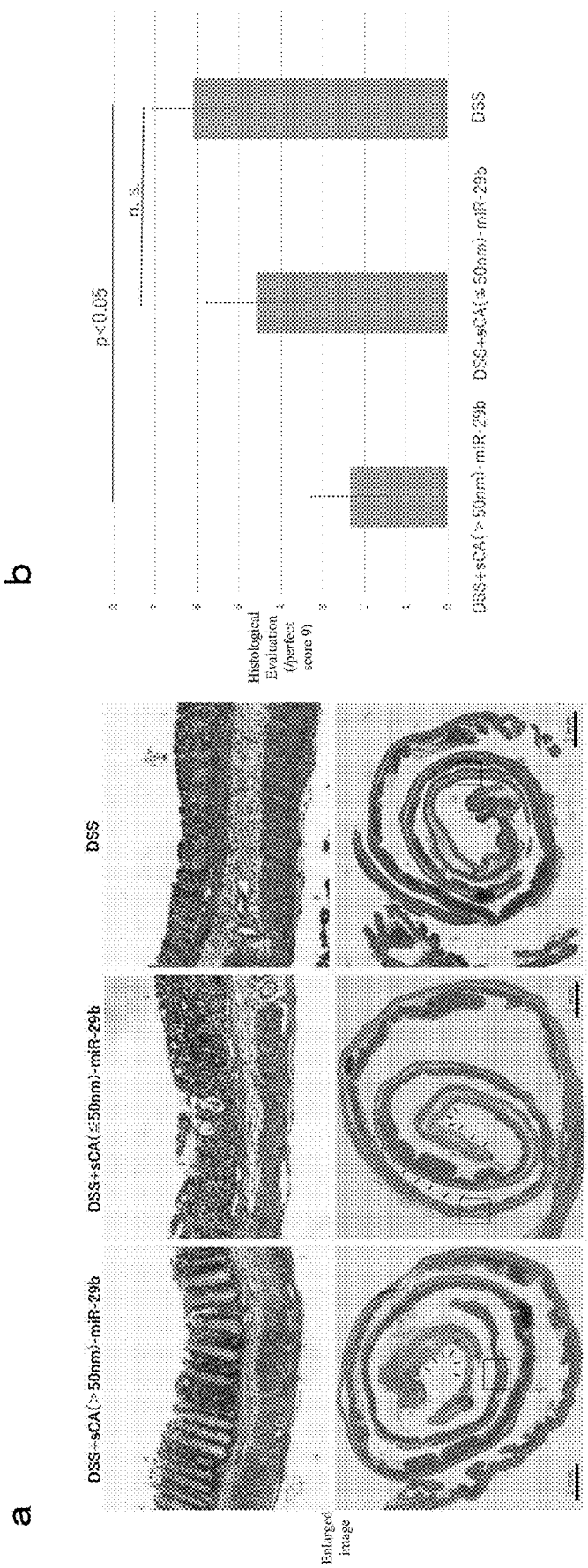
FIG. 12. (a) is a diagram illustrating a result of Test Example 6, which presents results of microscopically observing rectums stained with HE after intravenously administering the miR-29b/sCA composite (>50 nm) or the miR-29b/sCA composite (≤50 nm) to DSS-induced mouse enteritis models. (b) is a diagram illustrating a result of Test Example 6, which presents a result of histologically evaluating inflammations severities in the mouse large intestines.

FIG. 12, (a) presents results of observation with HE staining. As shown in FIG. 12, (a), in the DSS+sCA (>50 nm)-miR-29b group and the DSS+sCA (≤50 nm)-miR-29b group, degrees of destructions of the large intestine mucosal structures were lower than in the DSS group, and particularly in the DSS+sCA(>50 nm)-miR-29b group, the degree of destruction of the large intestine mucosal structure was remarkably lower than in the DSS+sCA (≤50 nm)-miR-29b group.

In addition, FIG. 12, (b) presents results of histologically evaluating inflammation severities. Also from the histological evaluation results, it was confirmed that the DSS+sCA (>50 nm)-miR-29b group showed a significant difference compared to the DSS group and had a remarkably high inflammation suppressive effect.

The above results demonstrated that the therapeutic effect for inflammatory bowel disease was further improved by using large particles having particle diameters of larger than 50 nm as the carbonate apatite for carrying the miR-29b.

Reference Test Example 3

Seven-week-old BALB/c mice (CLEA Japan, Inc.) were fed with water containing 2 wt % of DSS for 7 days to develop inflammatory enteritis, and to prepare DSS-induced mouse enteritis models. The Alexa647-miRNA/sCA composite was subcutaneously administered to the DSS-induced mouse enteritis models so that a dose of the miRNA was 60 μg/mouse. Four hours after administration of the Alexa647-miRNA/sCA composite, large intestines were taken from the mice to prepare frozen sections of rectal sites where the most intense inflammation was observed, which were immunostained using the anti-CD11c antibody and DAPI (CD11c is green), and fluoroscopically observed.

Figure 13:
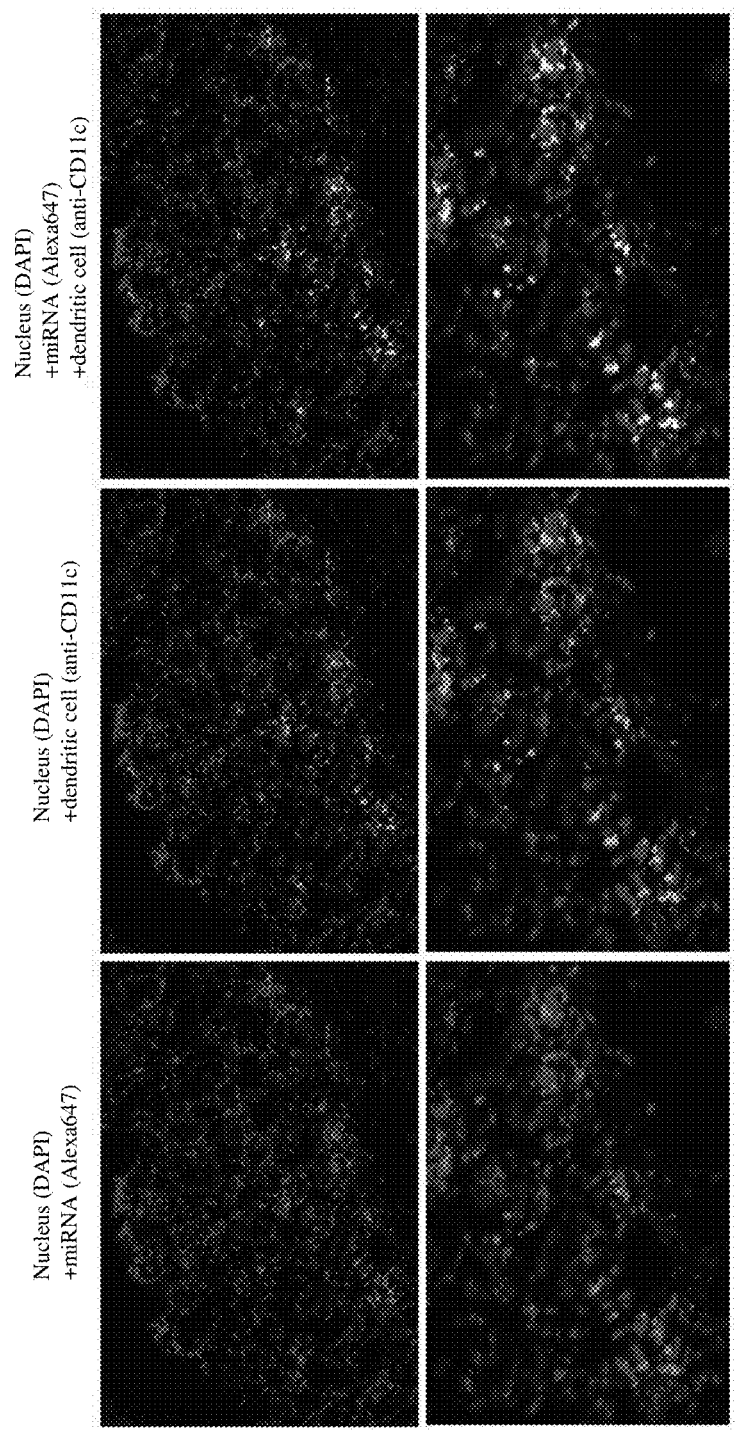
FIG. 13 presents images indicating results of fluoroscopically observing rectums immunostained with the anti-CD11c antibody and DAPI after subcutaneously administering the Alexa647-miRNA/sCA composite to DSS-induced mouse enteritis models, in Reference Test Example 3.

FIG. 13 presents results of fluoroscopically observing the immunostained frozen sections. As shown in FIG. 13, it was confirmed that distributions of the dark gray signals emitted by the Alexa647-miRNA and the light gray signals emitted by the anti-CD11c antibody were coincident with each other. That means, it was confirmed that even if subcutaneously administering the miRNA/sCA composite, the miRNA was efficiently taken into the dendritic cells and localized on an inflamed intestinal tract similarly to the case of intravenous administration.

Reference Test Example 4

Seven-week-old BALB/c mice (CLEA Japan, Inc.) were fed with water containing 2 wt % of dextran sulfate (DSS)

for 7 days to develop inflammatory enteritis, and to prepare DSS-induced mouse enteritis models. The MIRTX/sCA composite was subcutaneously administered to the DSS-induced mouse enteritis models so that a dose of the miRNA was 60 μg/mouse.

Four hours after administration of the MIRTX/sCA composite, the mice were sacrificed and the large intestines were taken out. Lamina propria cells were extracted from the colonic mucosas, and separated into CD11c-positive cells and CD11c-negative cells using the anti-CD11c antibody and autoMACS Pro Separator. RNAs were recovered from the obtained CD11c-positive cells and CD11c-negative cells respectively. Subsequently, a take-in level of the MIRTX in each intestinal tract was measured by quantitative RT-PCR. Note that the MIRTX was quantitatively determined as a relative value of the MIRTX level with respect to an RNU6B level, using a RNU6B as an internal standard.

In addition, for comparison's sake, the MIRTX was quantitatively determined under the same conditions as described above without administering the MIRTX/sCA composite.

Figure 14:
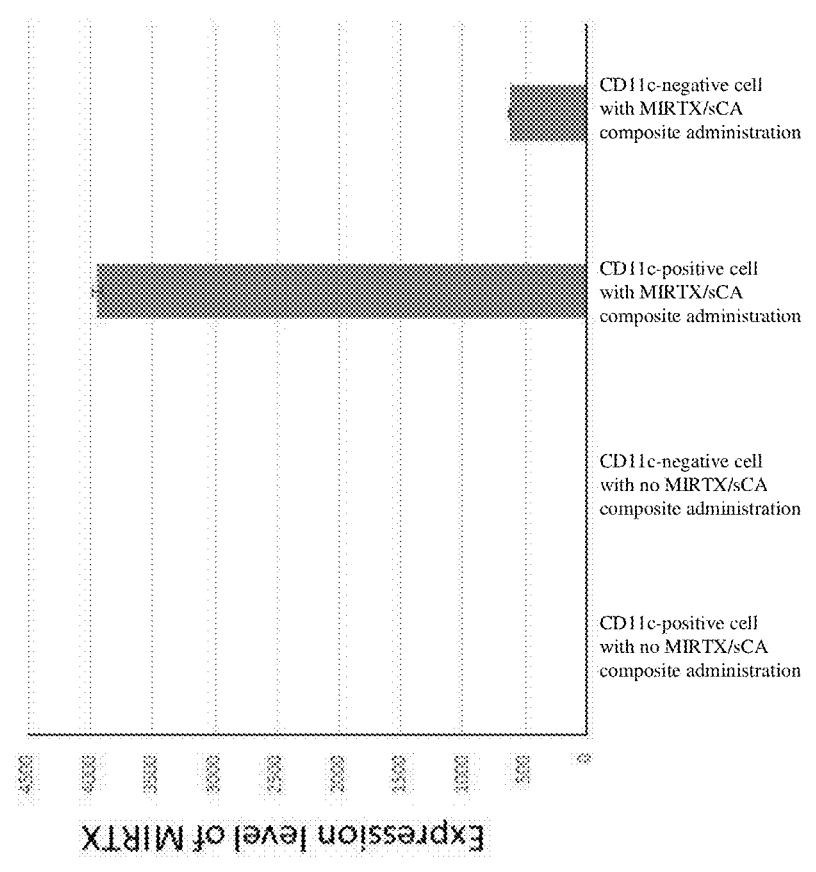

FIG. 14 presents the obtained result. As a result, when subcutaneously administering the MIRTX/sCA composite, a high MIRTX level was confirmed in the CD11c-positive cells, but the MIRTX level was low in the CD11c-negative cells. That means, also from this result, it was confirmed that when subcutaneously administering the miRNA/sCA composite, the miRNA was efficiently taken into the dendritic cells and localized on an inflamed intestinal tract.

Reference Test Example 5

Seven-week-old BALB/c mice (CLEA Japan, Inc.) were grouped into 4 groups (n=5 in each group) presented in Table 6. Under the conditions presented in Table 6, DSS and the miRNA/sCA composite were administered to the mice in each group.

TABLE 6

| Group | Condition of administration |
| --- | --- |
| Normal group | Mice were kept without administration of DSS and the miRNA/sCA composite for 9 days, and then sacrificed. |

TABLE 6-continued

| Group | Condition of administration |
| --- | --- |
| DSS group | Mice were fed with water containing 2 wt % of DSS for 7 days, then kept for 9 days, and sacrificed. (no miRNA/sCA composite administration) |
| DSS + sCA-NC-miR group | Mice were fed with water containing 2 wt % of DSS for 7 days. A starting date of DSS feed was designated as day 0, an NC-miR/sCA composite was locally administered to the mice in a transanal route so that a dose of the miRNA was 60 μg/mouse on day 1, 2, 3 and 5, and then the mice were sacrificed on day 9. |
| DSS + sCA-miR-29b group | Mice were fed with water containing 2 wt % of DSS for 7 days. A starting date of DSS feed was designated as day 0, a miR-29b/sCA composite was locally administered to the mice in a transanal route so that a dose of the miRNA was 60 μg/mouse on day 1, 2, 3 and 5, and then the mice were sacrificed on day 9. |

Body weights of the mice were measured from the onset to the end of the test. In addition, large intestines were recovered from the mice, lengths of the large intestines were measured, and the large intestines were stained with Hematoxylin-Eosin (HE) to microscopically observe states of inflammation. Furthermore, inflammation severities of the rectal sites where the most intense inflammation was observed were scored in the same manner as in Test Example 1 to determine a histological inflammation score.

Figure 15:
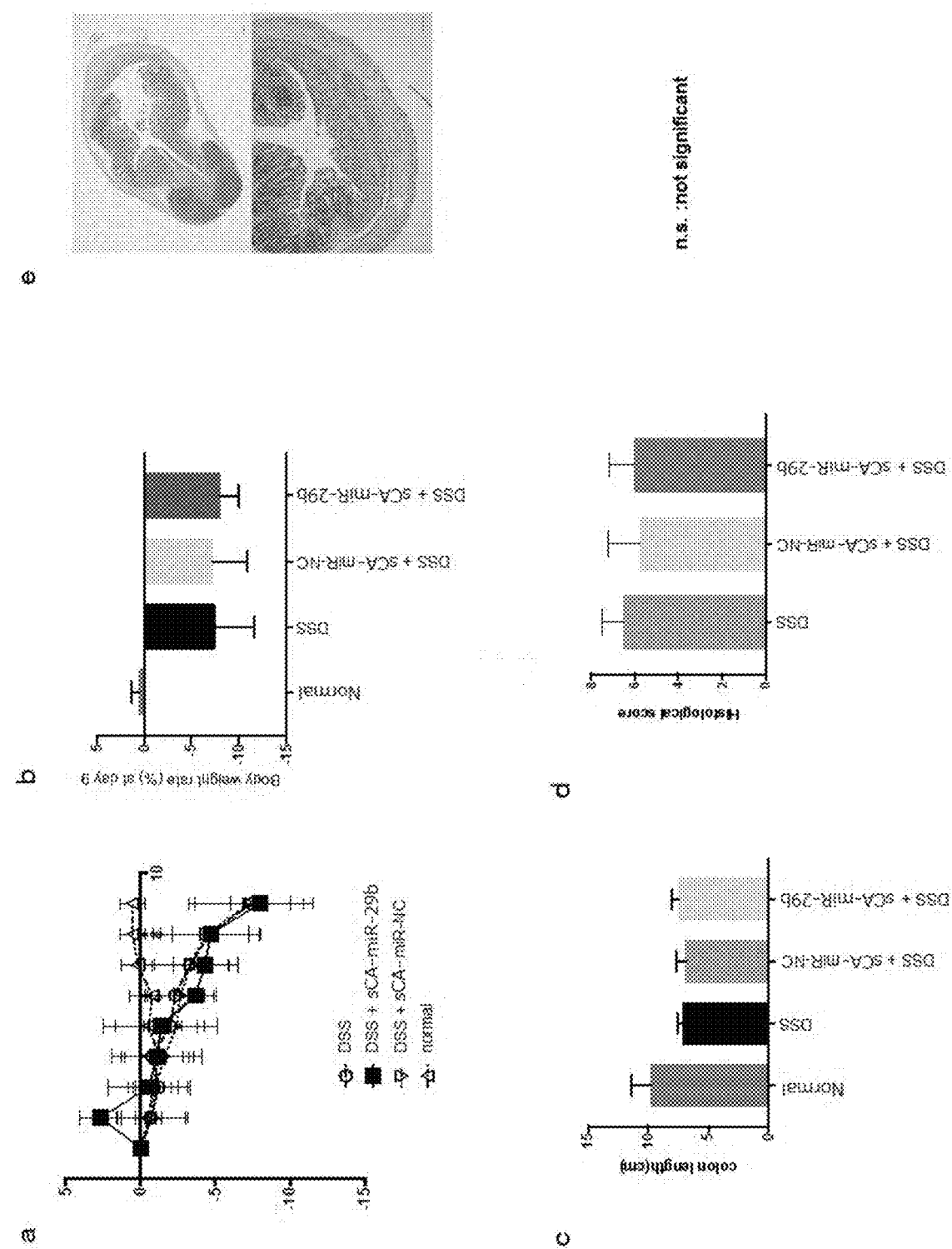
FIG. 15. (a) is a diagram illustrating a result of Reference Test Example 5, which presents a result of time-sequentially measuring body weights of mice to which DSS and various miRNA/sCA composites were locally administered. (b) is a diagram illustrating a result of Reference Test Example 5, which presents a result of measuring body weights of the mice at the end of the test. (c) is a diagram illustrating a result of Reference Test Example 5, which presents a result of measuring lengths of large intestines of the mice. (d) is a diagram illustrating a result of Reference Test Example 5, which presents a result of scoring rectal inflammation severities of the mice. (e) is a diagram illustrating a result of Reference Test Example 5, which presents results of microscopically observing rectums resected from the DSS+sCA-miR-29b group, and stained with HE.

FIG. 15, (a) presents a result of time-sequentially measuring body weights of the mice, and FIG. 15, (b) presents a result of measuring the body weights of the mice at the end of the test (day 9 from the onset of the miRNA/sCA composite administration). In addition, FIG. 15, (c) presents a result of measuring lengths of large intestines, and FIG. 15, (d) presents a result of the histological inflammation score. As a result, in the DSS+sCA-miR-29b group, suppression of mouse body weight loss, suppression of large intestine shortening, and lowering of the histological inflammation score were hardly observed similarly to the DSS group and the DSS+sCA-NC-miR group.

In addition, FIG. 15, (e) presents a result of observing a rectum stained with HE for the DSS+sCA-miR-29b group. Also from this result, it was confirmed that the colon inflammation was hardly improved in the DSS+sCA-miR-29b group.

That means, from this result, it was confirmed that even if locally administering the miR-29b/sCA composite for inflammatory bowel disease, the miR-29b/sCA composite showed little improvement effects.

The invention claimed is:

1. A method of treating an inflammatory bowel disease, comprising systemically administering composite particles having miR-29a and/or miR-29b carried on a carbonate apatite particle to a patient in need of treatment of the inflammatory bowel disease, wherein the carbonate apatite particles have an average particle diameter of 400 nm to 3000 nm, wherein the miR-29a and/or miR-29b is internalized into cells of an inflammatory bowel disease lesion and into dendritic cells localizing on a mucosa of the lesion, wherein the inflammatory bowel disease is effectively improved by an action of the miR-29a and/or miR-29b uptake directly into the cells of the lesion and by an action of the dendritic cells that have taken up the miR-29a and/or miR-29b.

2. The method according to claim 1, wherein the systemic administration is intravascular administration.

3. The method according to claim 1, wherein the composite particles comprise miR-29a.

4. The method according to claim 1, wherein the composite particles comprise miR-29b.

5. The method according to claim 1, wherein the composite particles comprise miR-29a and miR-29b.

6. The method according to claim 1, wherein the systemic administration is subcutaneous administration.

7. The method according to claim 1, wherein the carbonate apatite particles have an average particle diameter of greater than 50 nm and 3000 nm or smaller.

8. The method according to claim 1, wherein the miR-29a and/or miR-29b carried on the carbonate apatite particles is selected from the group consisting of a mature miRNA, a hairpin type precursor miRNA (pri-miRNA), and a pre-miRNA in which a part of the pri-miRNA is cleaved.

9. The method according to claim 1, wherein the miR-29a and/or the miR-29b are adsorbed to and carried on the carbonate apatite particle through an ionic bond or a hydrogen bond.

10. The method according to claim 1, wherein the inflammatory bowel disease is ulcerative colitis.

11. The method according to claim 1, wherein the inflammatory bowel disease is Crohn's disease.

* * * * *

SEQUENCE LISTING

<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1
uagcaccauc ugaaaucggu ua                22

<210> SEQ ID NO 2
<211> LENGTH: 22
<212> TYPE: RNA
<213> ORGANISM: Homo sapiens

```
<400> SEQUENCE: 2
uaaccgauuu cagauggugc ua                                          22

<210> SEQ ID NO 3
<211> LENGTH: 23
<212> TYPE: RNA
<213> ORGANISM: Homo sapiens

<400> SEQUENCE: 3
uagcaccauu ugaaaucagu guu                                         23

<210> SEQ ID NO 4
<211> LENGTH: 23
<212> TYPE: RNA
<213> ORGANISM: Homo sapiens

<400> SEQUENCE: 4
aacacugauu ucaaauggug cua                                         23

<210> SEQ ID NO 5
<211> LENGTH: 24
<212> TYPE: RNA
<213> ORGANISM: Artificial Sequence
<220> FEATURE:
<223> OTHER INFORMATION: Sence strand of artificial miRNA(MIRTX)

<400> SEQUENCE: 5
ucuaaaccac cauaugaaac cagc                                        24

<210> SEQ ID NO 6
<211> LENGTH: 24
<212> TYPE: RNA
<213> ORGANISM: Artificial Sequence
<220> FEATURE:
<223> OTHER INFORMATION: Antisense strand of artificial miRNA(MIRTX)

<400> SEQUENCE: 6
gcugguuuua uauggugguu uaga                                        24

<210> SEQ ID NO 7
<211> LENGTH: 19
<212> TYPE: RNA
<213> ORGANISM: Artificial Sequence
<220> FEATURE:
<223> OTHER INFORMATION: Sense strand of Alexa647-miRNA

<400> SEQUENCE: 7
auccgcgcga uaguacgua                                              19

<210> SEQ ID NO 8
<211> LENGTH: 19
<212> TYPE: RNA
<213> ORGANISM: Artificial Sequence
<220> FEATURE:
<223> OTHER INFORMATION: Antisense strand of Alexa647-miRNA

<400> SEQUENCE: 8
uacguacuau cgcgcggau                                              19

<210> SEQ ID NO 9
<211> LENGTH: 25
<212> TYPE: RNA
<213> ORGANISM: Artificial Sequence
<220> FEATURE:
<223> OTHER INFORMATION: Sense strand of NC-miR
```

```
<400> SEQUENCE: 9
uaaauguacc gcgcguggag aggaa                                          25

<210> SEQ ID NO 10
<211> LENGTH: 25
<212> TYPE: RNA
<213> ORGANISM: Artificial Sequence
<220> FEATURE:
<223> OTHER INFORMATION: Antisense strand of NC-miR

<400> SEQUENCE: 10
uuccucucca cgcgcaguac auuua                                          25
```